(12) United States Patent
Cervino

(10) Patent No.: US 10,793,911 B2
(45) Date of Patent: *Oct. 6, 2020

(54) HOST DNA AS A BIOMARKER OF CROHN'S DISEASE

(71) Applicant: ENTEROME, Paris (FR)

(72) Inventor: Alessandra Cristina L Cervino, Paris (FR)

(73) Assignee: ENTEROME, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/877,336

(22) Filed: Jan. 22, 2018

(65) Prior Publication Data

US 2018/0251844 A1    Sep. 6, 2018

Related U.S. Application Data

(63) Continuation of application No. 15/011,314, filed on Jan. 29, 2016, now Pat. No. 9,873,914.

(30) Foreign Application Priority Data

Jan. 30, 2015    (EP) ..................... 15305142

(51) Int. Cl.
    *C12Q 1/68*      (2018.01)
    *C12Q 1/6883*    (2018.01)

(52) U.S. Cl.
    CPC ..... *C12Q 1/6883* (2013.01); *C12Q 2600/106* (2013.01); *C12Q 2600/112* (2013.01); *C12Q 2600/136* (2013.01); *C12Q 2600/158* (2013.01)

(58) Field of Classification Search
    None
    See application file for complete search history.

(56) References Cited

U.S. PATENT DOCUMENTS

| 9,873,914 B2 * | 1/2018 | Cervino ............... C12Q 1/6883 |
| 2004/0259101 A1 | 12/2004 | Shuber |
| 2014/0186845 A1 | 7/2014 | Laurell et al. |

FOREIGN PATENT DOCUMENTS

| WO | 01/18252 A2 | 3/2001 |
| WO | 2001/18252 A2 | 3/2001 |
| WO | 2008/67195 A2 | 6/2008 |
| WO | 2009/065551 A1 | 5/2009 |
| WO | 2012/150453 A1 | 11/2012 |

OTHER PUBLICATIONS

Strausberg et al, in Microarrays and Cancer Research, 2002, Warrington et al (eds.), Eaton Publishing, Westborough, MA, pp. xi-xvi.*

Notterman et al, in Microarrays and Cancer Research, 2002, Warrington et al (eds.), Eaton Publishing, Westborough, MA, pp. 81-111.*

Anonymous: "GSN:BBL10513", Jul. 9, 2014, Retrieved from Internet: URL:http://ibis.internal.epo.org/exam/dbfetch.jsp48 d=GSN:BBL10513 [retrieved on Mar. 22, 2016] English Equivalent Abstract: CN103911440B (Univ. Nanjing Medical) Apr. 22, 2015 (Apr. 22, 2015).

Bjorkmana, J., et al., Differential Amplicons (deltaAmP)—A New Molecular Method to Assess RNA Integrity, Biomolecular Detection and Quantification, 2016, 6:4-12.

Cho, J.H., et al., Recent insights into the genetics of inflammatory bowel disease. Gastroenterology, 2011, 140 (6):1704-12.

Dhaliwal, A., et al., Utility of Faecal Calprotectin in Inflammatory Bowel Disease (IBD) What Cut-Offs Should We Apply?, Frontline Gastroenterol., 2015, 6(1):14-19.

Godon, J.J. et al., Molecular Microbial Diversity of an Anaerobic Digestor as Determined by Small-Subunit rDNA Sequence Analysis, Appl. Environ. Microbial., 1997, 63(7):2802-2813.

Heid, C.A., et al., Realtime quantitative PCR, Genome Research, 1996, 6:986-994.

Klaaseen, C.H., et al., Quantification of Human DNA in Feces as a Diagnostic Test for the Presence of Colorectal Cancer, Clinical Chemistry, American Association for Clinical Chemistry, Washington, DC, 2003, 49(7):1185-1187.

Kultima, J.R., et al., MOCAT: A Metagenomics Assembly and Gene Prediction Toolkit, PLoS One, 2012, 7(10): e47656.

Laas, et al., Diagnosis and classification of Crohn's disease, Autoimmun Rev., 2014, 13(4-5):467-71.

Laurell, H., et al., Correction of RT-qPCR Data for Genomic DNA-Derived Signals with ValidPrime, Nucleic Acids Research, 2012, 40(7):e51-e51.

Manichanh, L., et al. Reduced Diversity of Faecal Microbiota in Crohn's Disease Revealed by a Metagenomic Approach, Gut, 2006, 55:2015-211.

Methe, B.A., et al.; A framework for Human Microbiome Research, Nature, 2012, 486:215-221.

(Continued)

*Primary Examiner* — James Martinell
(74) *Attorney, Agent, or Firm* — Arrigo, Lee, Guttman & Mouta-Bellum LLP

(57) ABSTRACT

The invention relates to methods of analysing a sample from a subject having or suspected of having Crohn's disease for the abundance of the subject's nucleic acid (e.g., DNA) in the sample. The invention also relates to methods for measuring abundance of nucleic acid (e.g., DNA) in stool from a human subject having or suspected of having Crohn's Disease (CD). In various embodiments, an in vitro method includes analysing the relative abundance of the host (human) DNA in said sample of stool or nucleic acid extracted or isolated from a stool sample from the host (human); determining the relative abundance of the host (human's) DNA in the sample; and associating the abundance of the host (human) DNA with the host (human) providing the stool sample, or the host (human) providing the stool sample from which the nucleic acid was extracted.

7 Claims, 8 Drawing Sheets
Specification includes a Sequence Listing.

(56) References Cited

OTHER PUBLICATIONS

Molodecky, N.A., et al., Increasing Incidence and Prevalence of the Inflammatory Bowel Diseases With Time, Based on Systematic Review, Gastroenterology, 2012, 142(1):46-54.

Morgan, X.C., et al., Dysfunction of the Intestinal Microbiome in Inflammatory Bowel Disease and Treatment, Genome Biology, 2012, 13:R79, 18 pages.

Nn: ValidPrime(TM) Control for Genomic Background Human and Mouse Probe Protocol. Version 1.1, Sep. 1, 2012, Retrieved from Internet: URL:http://www.tataa.com/wp-content/uploads/2012/10/TATAA-Manual_ValidPrime_Probe_v01_1.pdf [retrieved on Mar. 22, 2016].

Papa, E., et al., Non-Invasive Mapping of the Gastrointestinal Microbiota Identifies Children with Inflammatory Bowel Disease, PLoS One, 2012, 7(6):E39242 pp. 1-12.

Parker, R.M., et al., mRNA: Detection by in Situ and Northern Hybridization, 1999, Methods in Molecular Biology, vol. 106: Receptor Binding Techniques, Humana Press, Inc. Totowa, New Jersey 07512, pp. 247-283.

Poullis, A., et al., Emerging Role of Calprotectin in Gastroenterology, Journal of Gastroenterology and Hepatology, 2003, 18(7):756-762.

Qin, J., et al., A Human Gut Microbial Gene Catalogue Established by Metagenomic Sequencing, Nature, 2010, 464 (4):59-67.

Reeves, J.R., et al., Methods in Molecular Medicine, vol. 39 Ovarian Cancer Methods and Protocols, 2000, Edited by J.M. S. Barlett Humana Press, Inc., Totowa NJ, pp. 471-483.

Schena, M., Protein Microarrays, 2005, Jones and Bartlett Publishers, Inc., ISBN 0-7637-3127-7.

Shewale, J.G., et al., Human Genomic DNA Quantitation System, H-Quant: Development and Validation for use in Forensic Casework, Journal of Forensic Science, 2007, 52(2):364-370.

Villa, E., et al., Identification of Subjects at Risk for Colorectal Carcinoma Through a Test Based on K-ras Determination in the Stool, Gastroenterology, 1996, 110(5):1346-1353.

Vincent, C., et al., Excretion of Host DNA in Feces Is Associated with Risk of Clostridium difficile Infection, Journal of Immunology Research, 2015, Article ID 246203, 7 pages, http://dx.doi.org/10.1155/2015/246203.

Japanese Intellectual Property Office, Office Action issued in corresponding Japanese Patent Application No. 2017-540126, dated Mar. 18, 2019, pp. 1-3.

Casellas et al., Fecal Excretion of Human Deoxyribonucleic Acid as an Index of Inflammatory Activity in Ulcerative Colitis, Clin. Gastroenterol. Hepatol. (2004) vol. 2, issue 8, p. 683-689.

* cited by examiner

SEQUENCE LISTING

```
<160> NUMBER OF SEQ ID NOS: 6

<210> SEQ ID NO 1
<211> LENGTH: 16
<212> TYPE: DNA
<213> ORGANISM: Artificial Sequence
<220> FEATURE:
<223> OTHER INFORMATION: Description Artificial Sequence: VP5 forward
      primer

<400> SEQUENCE: 1
aacttggtgc ggaggt                                                     16

<210> SEQ ID NO 2
<211> LENGTH: 18
<212> TYPE: DNA
<213> ORGANISM: Artificial Sequence
<220> FEATURE:
<223> OTHER INFORMATION: Description Artificial Sequence: VP5 reverse
      primer

<400> SEQUENCE: 2
atcgcttctg atggacac                                                   18

<210> SEQ ID NO 3
<211> LENGTH: 27
<212> TYPE: DNA
<213> ORGANISM: Artificial Sequence
<220> FEATURE:
<223> OTHER INFORMATION: Description Artificial Sequence: VP5 probe

<400> SEQUENCE: 3
ccgccagact gcaatccatc aatgaca                                         27

<210> SEQ ID NO 4
<211> LENGTH: 17
<212> TYPE: DNA
```

```
<213> ORGANISM: Artificial Sequence
<220> FEATURE:
<223> OTHER INFORMATION: Description Artificial Sequence: VP9 forward
      primer

<400> SEQUENCE: 4
gcggaaacac aagggaa                                                      17

<210> SEQ ID NO 5
<211> LENGTH: 20
<212> TYPE: DNA
<213> ORGANISM: Artificial Sequence
<220> FEATURE:
<223> OTHER INFORMATION: Description Artificial Sequence: VP9 reverse
      primer

<400> SEQUENCE: 5
ttagaggcaa aagcaaagaa                                                   20

<210> SEQ ID NO 6
<211> LENGTH: 27
<212> TYPE: DNA
<213> ORGANISM: Artificial Sequence
<220> FEATURE:
<223> OTHER INFORMATION: Description Artificial Sequence: VP9 probe

<400> SEQUENCE: 6
acagctaatt aaaattgcac agttcct                                           27
```

HOST DNA AS A BIOMARKER OF CROHN'S DISEASE

RELATED APPLICATION INFORMATION

This application is continuation application of application Ser. No. 15/011,314, filed Jan. 29, 2016, which claims the benefit of priority to European application no. 15305142.0, filed Jan. 30, 2015, all of which applications are expressly incorporated herein by reference in their entirety.

SEQUENCE LISTING

The instant application contains a Sequence Listing which has been submitted electronically in ASCII format and is hereby incorporated by reference in its entirety. Said ASCII copy, is named "ENTEROM-CON-0456349_ST25.txt" and 1,669 bytes in size.

TECHNICAL FIELD OF THE INVENTION

The invention relates to a new method for diagnosing patients with Crohn disease, and/or for diagnosing the status of the disease in Crohn-suffering patients.

INTRODUCTION

Crohn's disease (CD) is a chronic inflammatory bowel disease (IBD) that may affect any part of the gastrointestinal tract from mouth to anus. The age of onset is generally between 15-30 years and it is equally prevalent in women and men. The highest prevalence is found in Europe and North America with just over 300 per 100.000 persons (Molodecky et al. 2012). CD generally leads to abdominal pain, severe diarrhoea and weight disorders. The disease is of unknown aetiology and multifactorial: environmental factors, host genetics and gut microbiome have all been shown to impact the risk of disease and its severity (Cho, J. H., & Brant, S. R. (2011)).

The clinical diagnosis of CD is supported by serologic, radiologic, endoscopic, and histologic findings. Currently, there are no standalone laboratory developed tests that allow the diagnostic of CD. Amongst available laboratory tests, serum CRP, faecal calprotectin and lactoferrin are the most widely used markers, but they are not specific to CD. Disease activity can be measured by the Crohn's Disease Activity index (CDAI), a score resulting from the combination of multiple parameters or the Harvey-Bradshaw index (HBI) which only consists of clinical parameters (Laas et al. 2014).

Moreover, in patients diagnosed with CD, monitoring clinical symptoms alone is not reliable enough to assess disease activity. Patients self-reporting low disease activity often present intestinal lesions during an endoscopic exam. Biological markers, such as faecal calprotectin, are useful, but nonspecific and their increase is associated with systemic/mucosal inflammation at the late onset of the flare. Endoscopy enables to detect mucosal healing, which is considered as the most robust and reliable sign of disease remission; however, routine repeated endoscopic monitoring is not feasible, because of the required bowel preparation and general anaesthesia. New imaging tools, such as MRI, have been shown to be effective, but it is expensive, time-consuming, and limited access precludes routine use. The MR Enterography, presented as the most promising approach, implies also bowel preparation and invasive colonoscopy.

The tight control of CD, through accurate surveillance and treatment adjustment, is thus a key in the management of such patients, because of the recurring and remitting nature of these disorders. Yet, none of the current diagnostic methods is satisfactory, for the above-mentioned reasons.

Patients and healthcare providers are therefore actively looking for non-invasive tools enabling evaluation of disease activity and monitoring of patients care.

More precisely, there remains a need to identify a biomarker of CD that would allow diagnosing the disease in a patient that is non-invasive, simple and accurate manner. This is precisely the subject of the present invention.

Also, there is a need for identifying a biomarker which could help in distinguishing between patients suffering from an active CD vs. from a quiescent stage of said disease. Indeed, this information could help clinicians in diagnosing the stage of CD, predicting the occurrence of said changes, in order to choose from the different treatment options (intensive or conventional), without having to perform an endoscopic analysis. This need is fulfilled by the present invention.

Increase of host DNA in stool samples of patients suffering from diseases known to induce an inflammatory state of the gut mucosa has been observed in the prior art.

In a prospective cohort of 599 hospitalized patients, a single rectal swab was obtained from each patient within 7 days of admission to the hospital. Host DNA proportions were negatively correlated with intestinal microbiota diversity. *Enterococcus* and *Escherichia* were enriched in patients excreting high quantities of human DNA, while Ruminococcus and Odoribacter were depleted. The quantification of human DNA in faeces could serve as a simple and non-invasive approach to assess bowel inflammation (Vincent et al, 2014).

Stool samples from colorectal cancer patients also contain increased concentrations of human DNA (Klaassen et al 2003).

The amount of host DNA in stool samples of Crohn suffering patients has never been assessed so far. Yet, it has been observed that stool samples from CD patients also contained increased concentrations of human DNA. This is very surprising since the total area of intestinal lesions is low in CD patients (as compared with ulcerative colitis) and visible bleeding in the faeces is quite uncommon in Crohn's disease.

The present inventors analysed, by a quantitative metagenomic analysis, but also by qPCR, the human DNA abundance in a number of stool samples that have been collected from healthy controls and CD patients. Moreover, the host DNA abundance was assessed in stool samples obtained from patients suffering from aggressive Crohn disease vs. from a quiescent stage of said disease.

In so doing, the present inventors observed that the presence and quantity of human DNA into stool samples are markers of Crohn's disease, and that patients suffering from aggressive Crohn disease vs. from a quiescent stage of said disease can be discriminated using this very same biomarker.

To sum up, they demonstrated that the presence of host DNA in the faeces of CD patients may be used as a biomarker of CD, of its activity or severity.

SUMMARY

Provided herein are methods of analysing a sample from a subject having or suspected of having Crohn's disease for the abundance of the subject's DNA in the sample. In one embodiment, a method includes providing a biological sample from a subject (e.g., human); determining the relative abundance of the subject's (e.g., human's) DNA in the sample; and comparing the relative abundance of the subject's (e.g., human's) DNA in the sample to a reference value and determining if the relative abundance of the subject's (e.g., human's) DNA in the sample is higher than the reference value.

Also provided herein are methods for measuring abundance of DNA in stool from a human having or suspected of having Crohn's Disease (CD). In one embodiment, a method includes providing a sample of stool or nucleic acid extracted or isolated from a stool sample from the human; determining the relative abundance of the human's DNA in the sample; and associating the abundance of the human DNA with the human providing the stool sample, or the human providing the stool sample from which the nucleic acid was extracted.

Further provided herein are methods for generating quantitative data and methods for generating a quantitative data set for a subject (e.g., human) that has or is at risk of having Crohn's Disease (CD).

In one embodiment, a method includes performing at least one assay to determine the abundance of the subject's (e.g., human's) DNA in a sample from the subject (e.g., human) to generate a first dataset comprising the quantitative data, wherein the quantitative data represents the relative abundance of the subject's (e.g., human's) DNA in the sample, optionally compared to a reference value.

In another embodiment, a method includes providing a stool sample from a subject (e.g., human) or nucleic acid extracted or isolated from a stool sample of a subject that has or is suspected of having Crohn Disease; transforming the stool sample or nucleic acid extracted or isolated from the stool sample into an analytical composition comprising copies of the subject's DNA, wherein the copies comprise one or more primers or probes; determining a relative abundance of the subject's DNA in the stool sample or nucleic acid extracted or isolated from the stool sample; optionally determining a calprotectin level for the stool sample or nucleic acid extracted or isolated from the stool sample; and optionally determining a Harvey-Bradshaw index (HBI) score for the subject, where the quantitative dataset comprises the relative abundance of the subject's DNA; and/or optionally the calprotectin level and/or the HBI score.

Moreover, provided herein are amplification methods of measuring the abundance of a target nucleic acid sequence in a sample. In one embodiment, a method includes:
contacting a sample from a subject having or suspected of having Crohn's Disease (CD) comprising a target nucleic acid sequence with a set of oligonucleotide primers, each primer comprising a 5' end and a 3' end, wherein a first primer comprises a sequence complementary to a first region in the target nucleic acid sequence, and a second primer comprises a sequence complementary to a second region in the target nucleic acid sequence, wherein the second region is downstream of the first region;
further contacting the sample with deoxynucleotide triphosphates (dNTPs), thereby forming a mixture;
allowing the first and second oligonucleotide primers to anneal to the target nucleic acid sequence of a) thereby forming an oligonucleotide primer annealed target nucleic acid;
exposing the oligonucleotide primer annealed target nucleic acid of step c) to a template-dependent polymerizing agent having 5' to 3' polymerization activity under conditions permissive for amplification, and whereby the oligonucleotide primers are extended to produce extension products; and detecting the extension products, thereby measuring the abundance of the target nucleic acid sequence in the sample.

Additionally, provided herein are reaction solutions, such solutions optionally contained in a vessel. In one embodiment, a reaction solution includes: a polymerizing agent that synthesizes or amplifies nucleic acid; a sample comprising stool or DNA extracted or isolated from stool of a subject (e.g., human) having or suspected of having Crohn's Disease (CD); oligonucleotide primers or oligonucleotide probe designed to specifically hybridize to a target sequence of the subject's DNA; deoxynucleotide triphosphates (dNTPs); and
buffers or other agents permissive for detection, replication or amplification of the target sequence. Such reaction solutions may be a part of the methods and compositions set forth herein, for example, for amplification of a target sequence, for example, for analysing a sample for the abundance of the subject's (e.g., human's) DNA in the sample.

In various aspects of the invention methods herein, performance of an assay or analysis includes: providing or obtaining a sample (e.g., stool) from a subject such as a human, where the sample includes the subject's DNA; contacting the sample with a detectable reagent; generating a distinct complex between the detectable reagent and the subject's DNA; and detecting the complex to generate the quantitative data.

Still further provided are embodiments distinct from or aspects in addition to the invention methods, compositions, kits and reaction solutions set forth herein. Such embodiments and aspects can be used alone or in any combination with each other.

In particular, for example, a sample may be stool, or nucleic acid extracted or isolated from stool.

In particular, for example, the abundance of the subject's DNA is determined by quantitation of a genomic DNA sequence.

In particular, for example, the abundance of the subject's DNA is determined by quantitation of a non-transcribed region or locus of genomic DNA.

In particular, for example, the abundance of the subject's DNA is determined by quantitation of a single copy per haploid genomic DNA sequence.

In particular, for example, abundance of the subject's DNA is determined by quantitative polymerase chain reaction (qPCR).

In particular, for example, classifying the subject or human, based upon the relative abundance of the DNA in the sample being higher or lower than the reference value.

In particular, for example, the subject or human is classified if the relative abundance of the DNA in the sample is higher than the reference value.

In particular, for example, classifying the subject or human, if the relative abundance of the DNA in the sample is higher than the reference value and the amount of calprotectin in the sample is higher a second reference value.

In particular, for example, determining the amount of calprotectin in the sample (e.g., stool, or nucleic acid extracted or isolated from stool).

In particular, for example, a sample that is not from a subject that has colon cancer or a bacterial infection; and/or a sample that is not from a subject that has a *Clostridium difficile* infection.

In particular, for example, the method is not for diagnosis of colon cancer or a bacterial infection; and/or not for diagnosis of a *Clostridium difficile* infection.

In particular, for example, the subject has symptoms associated with Crohn's Disease (CD). In particular aspects, representative non-limiting CD symptoms include: mucosal inflammation, mucosal ulcerations, or enhanced level of inflammation markers such as platelet count, mean platelet volume, erythrocyte sedimentation rate (ESR), serum thrombopoietin, serum erythropoietin, C-reactive protein, orosomucoid ($\alpha_1$-acid glycoprotein), TNF$\alpha$, Interleukins (e.g., IL1, IL2, IL6, IL8, IL10, IL15) lactoferrin or calprotectin.

In particular, for example, the subject has been diagnosed with Crohn's Disease (CD).

In particular, for example, the subject has been or is currently being treated for Crohn's Disease (CD).

In particular, for example, the subject has Crohn's Disease in an unstable state.

In particular, for example, the subject has Crohn's Disease in a stable state.

Additional embodiments and aspects of the invention are set forth below, which are appropriate alone or in combination with the above embodiments and aspects.

DETAILED DESCRIPTION

Figure 1:
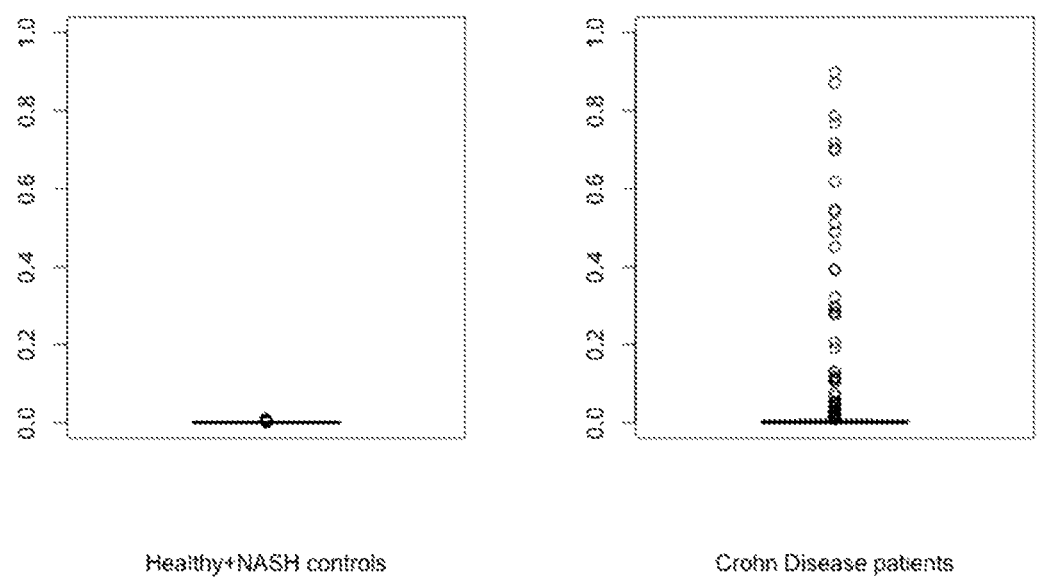
FIG. 1 discloses the Boxplots of the percent human DNA found in stool samples from healthy and NASH controls (on left) and Crohn Disease patients (on the right).

Methods of Measures, in Particular to Diagnose CD

In a first aspect, the present invention relates to a method for generating quantitative data for a subject having or suspected of having Crohn disease (CD), said method comprising: performing at least one assay to determine host DNA relative abundance in a biological sample from said subject, wherein the quantitative data represents host DNA relative abundance preferably compared to a reference value.

In other words, the invention relates to an in vitro method for analysing a biological sample from a subject having or suspected of having Crohn disease (CD), said method comprising:
a) Obtaining a biological sample from said subject,
b) Determining the relative abundance of host DNA in said sample,
and,
c) Determining if said relative abundance is higher than a reference value.

More precisely, the present invention relates to an in vitro method for diagnosing Crohn disease (CD) in a subject, said method comprising:
a) Obtaining a biological sample from said subject,
b) Determining the relative abundance of host DNA in said sample,
and,
c) Diagnosing that said subject suffers from Crohn disease, if said relative abundance is higher than a reference value.

This method is advantageous over the prior art diagnosis method as it is non-invasive, economically acceptable, and present a high specificity.

In some embodiments a method comprises generating a quantitative dataset for a subject, for example, by analysing or performing an assay from one or more samples obtained from the subject. A quantitative dataset can be a combined dataset (e.g., a collection of data) comprising one or more data obtained from one or more samples obtained from the same subject. In certain embodiments, a quantitative dataset comprises quantitative data obtained from a sample obtained from stool.

As used herein, the term "host DNA" refers to the DNA of the host of the gut microbiota, as opposed to microbial or viral DNA. If the tested subject is a human patient, then the term "host DNA" refers specifically to "human DNA".

DNA can be extracted from said biological sample of interest for example by using the extraction protocol described in Godon J J. et al., 1997. Other protocols can nevertheless be used and are well-known. Of note, the microbial DNA and the host DNA do not need to be physically separated for subsequent analysis.

Mammal DNA can be distinguished from microbial DNA by any conventional mean, such as detection of CpG methylation or of the bacterial 16S ribosomal DNA. It is also possible to use qPCR targeting the ALU (STR) repeat regions in human DNA, or the Beta-globulin, Beta-actin, and hTERT genes (Klaassen C H W et al, 2003; Shewale J G et al, *Journal of Forensic Science*, 2007, vol. 52(2)). Nanostring technologies could be also useful.

Quantification of the host and microbial DNA can be performed by any well-known method. The most commonly used methods known in the art for the quantification of DNA strands in a sample include Northern blotting and in situ hybridization (Parker & Barnes, *Methods in Molecular Biology* 106:247-283 (1999)) PCR-based methods, such as quantitative polymerase chain reaction (qPCR) (Heid et al., *Genome Research* 6:986-994 (1996)), and nucleic-acid based multiplex techniques, such as multiplex PCR and DNA microoarrays. Alternatively, antibodies may be employed that can recognize sequence-specific duplexes, including DNA duplexes or DNA-protein duplexes. Representative methods for sequencing-based analysis include chain-termination methods, shotgun sequencing methods, de novo sequencing, next generation sequencing methods (including Massively Parallel Signature Sequencing (MPSS), Polony sequencing, 454 pyrosequencing, Illumina (Solexa) sequencing, SOLiD sequencing, Ion semiconductor sequencing, DNA nanoball sequencing, Helioscope single molecule sequencing, Single molecule real time (SMRT) sequencing, RNAP sequencing, Nanopore DNA sequencing, Sequencing by hybridization and Microfluidic Sanger sequencing).

As used herein, a polymerizing agent having 5' to 3' polymerization activity is typically a protein that can catalyse/synthesize polymers of nucleosides or nucleotides. Such synthesis may require a template nucleic acid, which results in synthesis of the sequence complementary to the nucleic acid template. Specific non-limiting examples of polymerizing agents having 5' to 3' polymerization activity include a heat stable polymerase, such as Taq polymerase.

As shown in the examples below, it is also possible to measure host DNA from a pool of DNA by i) sequencing the DNA present in stool samples using high throughput sequencing technologies and ii) by aligning the short reads obtained by means of these sequencing technologies to the human genome. In this case, "relative abundance of host DNA" can be calculated by counting the number of reads mapped to a single reference sequence from the human genome (H) and the remaining number of reads generated (B), and normalizing the number of reads H by the total amount of reads (H+B).

As meant herein, the term "host DNA abundance" refers to the relative amount of host DNA as compared with the total amount of DNA present in said sample (including in particular bacterial and fungal DNA). In the present application, it will therefore preferably be referred to as "relative abundance" (or "relative amount") of host DNA.

Preferably, the host DNA abundance is measured by qPCR with human specific nucleic acid fragments, such as primers and/or probes.

As used herein, the term "nucleic acid", "nucleic acid sequence", "nucleotide", "nucleotide sequence", which are interchangeable, refer to a precise succession of natural nucleotides (e.g., A, T, G, C and U), corresponding to a single-stranded or double-stranded DNA such as cDNA, genomic DNA, ribosomal DNA or plasmidic DNA, and the transcription product of said DNA, such as RNA. A nucleic acid according to the invention may be isolated and prepared by any known method including, but not limited to, any synthetic method, any recombinant method, any ex vivo generation method and the like, as well as combinations thereof.

The probes and primers required or useful to carry out the qPCR on host DNA are referred herein as "nucleic acid fragments" in the context of the invention.

By "nucleic acid fragment", it is more generally meant herein a nucleic acid hybridizing to a nucleic acid of interest. For instance, such nucleic acid fragment may be at least 10 nucleotides in length or preferably, at least 15 nucleotides in length. They may also be at least 25 or at least 50 nucleotides in length.

Nucleic acid fragments according to the invention are specific to host DNA, and preferably to human host DNA, as they allow the discrimination of host DNA from other DNA present in the biological sample (i.e. non host DNA), such as fungal and/or bacterial DNA (i.e. microbial DNA). In other words, the nucleic acid fragments of the invention will hybridize to host DNA, but not (or essentially not) bind to a substantial part of the other DNA present in the biological sample (i.e. non host DNA), such as fungal and/or bacterial DNA (i.e. microbial DNA).

In the context of the present invention, the nucleic acid fragment will preferably hybridize to the host DNA under stringent hybridization conditions. One example of stringent hybridization conditions is where attempted hybridization is carried out at a temperature from about 50° C. to about 65° C., more preferably from about 55° C. to about 65° C., using a salt solution which can be e.g. about 0.9 molar. However, the skilled person will be able to vary such conditions in order to take into account variables such as the nucleic acid fragment length, base composition, type of ions present, etc A "primer" more specifically refers to a nucleic acid fragment that serves as a starting point for amplification of a nucleic acid of interest, i.e. herein of host DNA. Examples of nucleic primers of the invention include, but are not limited to, the primers of sequence SEQ ID NO:1, SEQ ID NO:2, SEQ ID NO:4 and SEQ ID NO:5. Such primers can be used in "a primer set" to amplify host DNA. Examples of primer set of the invention include, but are not limited to, the primer sets (SEQ ID NO:1, SEQ ID NO:2), and (SEQ ID NO:4, SEQ ID NO:5).

A "probe" more specifically refers to a nucleic acid fragment that can be used for detection of a nucleic acid of interest, i.e. herein of host DNA. This term encompasses various derivative forms such "fluorescent probe". When used in combination with a primer set as defined above, said probe can be used for quantification of a nucleic acid of interest. Examples of probes of the invention include, but are not limited to, the probes of sequence SEQ ID NO:3, and SEQ ID NO:6. Probes may be labelled by isotopes, radio-labels, binding moieties such as biotin, haptens such as digoxygenin, luminogenic, mass tags, phosphorescent or fluorescent moieties, or by fluorescent dyes alone (e.g., MGB, FAM, VIC, TET, NED, TAMRA, JOE, HEX, ROX, etc) or in combination with other dyes. These labels provide signals detectable by fluorescence, radioactivity, colorimetry, gravimetry, X-ray diffraction or absorption, magnetism, enzymatic activity, mass spectrometry, binding affinity and the like, and facilitate the detection or quantification of the nucleic acid of interest A "detectable reagent" may be incorporated into or bound to the detected product, by way of, for example, covalent or non-covalent bonding (e.g., van der Waals forces, ionic bonds, hydrophobic bonds, hydrogen bonding, etc.). In the context of the invention, primers, probes and other nucleic acids may be considered as non-limiting examples of detectable reagents. Other non-limiting examples of detectable reagents include proteins, such as antibodies. A "complex" can be used to refer to the binding between a detectable reagent and a target, such as host/human nucleic acid (e.g., RNA or DNA), and is typically a non-naturally occurring entity formed by the interaction.

An analytical composition often comprises elements, matter and/or components not found in nature. In certain embodiments, an analytical composition comprises matter made by the hand of man, non-limiting examples of which include copies of nucleic acids (e.g., RNA or DNA, e.g., amplicons generated in vitro often by use of a polymerizing agent), probes, primers and/or detectable reagents, nucleotide analogues, disproportionate quantities of nucleic acid (e.g., amounts and ratios of nucleic acid fragments (e.g., copies and/or amplicons) not found in nature (e.g., in a cell or an organism), nucleic acid in a partially pure or purified form which form excludes other biological cell components (e.g., whole cells, eukaryotic or prokaryotic), proteins (e.g., histones), serum, blood, carbohydrates, bacterial cell walls, organelles, lipid, etc.).

In a preferred embodiment of the invention, host DNA abundance is measured by quantitative PCR (qPCR) by using at least one nucleic acid fragment selected from the group of nucleic acid fragments of sequence SEQ ID NO:1 to SEQ ID NO:6, variants thereof and complementary sequences thereof.

More preferably, host DNA abundance is measured by quantitative PCR (qPCR) by using the primer set (SEQ ID NO:1, SEQ ID NO:2) combined with the probe of sequence SEQ ID NO:3, and/or by using the primer set (SEQ ID NO:4, SEQ ID NO:5) combined with the probe of sequence SEQ ID NO:6.

The term "complementary" means that, for example, each nucleotide of a first nucleic acid sequence is paired with the complementary base of a second nucleic acid sequence whose orientation is reversed. Complementary nucleotides are A and T (or A and U) or C and G.

"Variants" of a nucleic acid fragment according to the present invention include, but are not limited to, nucleic acid sequences which are at least 99% identical after alignment to said nucleic acid fragment and retain their capacity to hybridize to a nucleic acid of interest, herein to host DNA. Examples of variants are degenerate nucleic acid fragments.

The methods of the invention can be applied to any subject, either human or animal. Yet, in a preferred embodiment, it is applied to a human patient, in particular to a human that is suspected of suffering from CD, or is in need of a confirmation of having CD. More precisely, the method of the invention is useful for monitoring human patients showing enhanced level of inflammation markers such as platelet count, mean platelet volume, erythrocyte sedimentation rate (ESR), serum thrombopoietin, serum erythropoietin, C-reactive protein and orosomucoid ($\alpha_1$-acid glycoprotein), TNF$\alpha$, Interleukins (notably IL1, IL2, IL6, IL8, IL10, IL15) as well as fecal markers of inflammation such as lactoferrin and calprotectin. Precise methods for diagnosing CD are detailed in Laas et al, 2014, which is incorporated herein by reference. More preferably, the subject is not suffering from at least one of the following pathologies: cancer or precancer, more particularly from colon cancer, colorectal cancer or colorectal adenoma, ulcerative colitis, microscopic colitis (such as collagenous colitis or lymphocytic colitis), ischaemic colitis, diversion colitis, allergic colitis, Behcet's disease, colorectal polyps, celiac disease, irritable bowel syndrome (IBS), and any combination thereof.

In a preferred embodiment, the biological sample used in step a) of the method invention is a stool sample. Indeed, such a sample may be obtained by a completely harmless collection from the patient. Preferably, said stool sample is collected and stored in appropriate buffers that do not denature or affect the DNA contained in same (in this aim, one can use, e.g., the RNA Later® RNA stabilization Reagent (Ambion), or the Stool DNA Stabilizer (Invitek), or a mix of EDTA and DMSO). More preferably, the samples are stored at −80° C. until DNA extraction and subsequent analysis.

As used herein, the term "reference value" refers to a specific value or dataset that can be used to identify samples that are known to be poor in host DNA or to identify samples having stable CD. In some embodiments, a reference value is obtained for example from historical abundance data obtained for healthy subjects. In some embodiments, a reference value is obtained from historical abundance data obtained for a patient or a pool of patients having been diagnosed unambiguously for a stable CD. In this example, a reference value can be obtained by measuring the relative abundance of host DNA in stool samples from patients being in a stable state of CD. It can be a single cut-off value, such as a median or mean. It can be a single number, equally applicable to every sample. In a preferred embodiment, this reference value is a predetermined value. For healthy subjects a predetermined value is of about 1%. For subjects with stable CD, a predetermined value is of about 10%.

In principle, stool samples of healthy subjects are devoid of host DNA. Therefore, the presence of host DNA in the stool samples of a subject is a hint that said subject may suffer from a gut related disease. The present invention also encompasses all methods aimed at diagnosing CD in a subject, involving the detection of the presence of host DNA in stool samples. In other words, any diagnostic method involving the use of host DNA as biomarker of CD is encompassed within the present invention.

In the context of the invention, it is meant that the relative abundance of host DNA for the tested subject is "higher than a reference value" if it is superior, preferably 10 folds, and more preferably 20 folds superior to said reference value. In a preferred embodiment, it can be concluded that the tested subject is suffering from CD if the relative abundance of host DNA, as defined above, is higher than 1%, preferably higher than 10%, more preferably higher than 20%.

In other terms, the amount of host DNA is compared with a reference value. Said comparison can be done by those skilled in the art using statistical methods, in particular a ROC curve can be used to determine an optimal cut-off for sensitivity and specificity.

Comparison of host DNA abundance profile of a given subject with a reference value can be performed using statistical models or machine learning methods, whose aim is to predict a clinical response (e.g., 0 Mucosal Healing, 1 Mucosal Ulceration) based on a combination of the explanatory variables (amounts of host, e.g., human) DNA and calprotectin). Particular statistical models such as logistic regression and fisher linear discriminant analysis are relevant to predict outcome. Other discriminating algorithms include kNN (k nearest neighbour), decision trees, SVM (support vector machine), NN (neural networks) and forest In a particular embodiment, the method of the invention comprises: performing at least one assay to determine host DNA relative abundance in a stool sample from a subject having or suspected of having Crohn disease (CD), wherein the quantitative data represents host DNA relative abundance preferably compared to a reference value of about 1%.

In other words, the invention relates to an in vitro method for analysing a biological sample from a subject having or suspected of having Crohn disease (CD), said method comprising:
a) Obtaining a stool sample from said subject,
b) Determining the relative abundance of host DNA in said sample,
and,
c) Determining if said relative abundance is higher than a reference value of about 1%.

More precisely, in this particular embodiment, the method of the invention comprises the following steps:
a) Obtaining a stool sample from a human patient,
b) Determining the relative abundance of human DNA in said sample, by any conventional means disclosed above, and,
c) Diagnosing that said patient suffers from Crohn disease, if said relative abundance is higher than about 1%.

Methods of Measures, in Particular to Monitor the States of CD

In another aspect, the present invention relates to a method for generating quantitative data for a subject having or suspected of having Crohn disease (CD) in an unstable state, said method comprising: performing at least one assay to determine host DNA relative abundance in a biological sample from said subject, wherein the quantitative data represents host DNA relative abundance preferably compared to a reference value.

In other words, the invention relates to an in vitro method for analysing a biological sample from a subject having or suspected of having Crohn disease in an unstable state, said method comprising the steps of:
a) Obtaining a biological sample from said subject,
b) Determining the relative abundance of host DNA in said sample, and,
c) Determining if said relative abundance is higher than a reference value.

In a preferred embodiment, said reference value is of about 10%.

The present invention further relates to a method for generating quantitative data for a subject having or suspected of having Crohn disease (CD) in a stable state, said method comprising: performing at least one assay to determine host DNA relative abundance in a biological sample from said subject, wherein the quantitative data represents host DNA relative abundance preferably compared to a reference value.

In a preferred embodiment, said reference value is of about 1%.

In other words, the invention relates to an in vitro method for analysing a biological sample from a subject having or suspected of having Crohn disease in a stable state, said method comprising the steps of:
a) Obtaining a biological sample from said subject,
b) Determining the relative abundance of host DNA in said sample, and,
c) Determining if said relative abundance is lower than a first reference value and higher than a second reference value.

In a preferred embodiment, said first reference value is of about 10%, and said second reference value is of about 1%.

More particularly, the results obtained by the inventors allowed to identify a biomarker (host DNA) allowing to distinguish between patients suffering from an inactive (quiescent state) Crohn disease from patients suffering from aggressive Crohn disease (state associated with an imminent flare period), in particular in a non-invasive manner. Their results are consequently of peculiar value with regard to monitoring the stage of this disease.

In the context of the invention, "stable" patients are defined as CD patients for whom disease activity is stable over several weeks (patient in a "stable state"). While "unstable" patients (or patient "in an unstable state") are CD patients who had their treatment changed or intensified in the following weeks, whose blood tests showed/shows elevated activity in the following weeks, and/or whose self-evaluation showed/shows decreased health and/or had/have elevated calprotectin levels in consecutive samples, and/or who had/have systemic mucosal inflammation, more particularly systemic mucosal ulcerations. Stable or unstable can also be defined based on colonoscopical scores such as CDEIS or SES-CD.

Accordingly, the present invention more particularly targets a method aiming at diagnosing these two particular states in a subject suffering from CD.

More precisely, the present invention relates to an in vitro method for diagnosing the activity of the Crohn Disease in a subject, said method comprising the steps of:
a) Obtaining a biological sample from said subject,
b) Determining the relative abundance of host DNA in said sample, and,
c) Diagnosing that said subject has a Crohn Disease in an unstable state, if said relative abundance is higher than a reference value.

The above methods are advantageous over the prior art as they are non-invasive, economically acceptable, and present high specificity.

All the embodiments disclosed above, in particular for the diagnostic method of the invention, also applies to the present methods, notably aimed at monitoring the activity of the Crohn disease.

In particular, said subject can be a human patient that is suspected of suffering from CD, or is in need of a confirmation of having CD or has been diagnosed with CD. More precisely, the methods of the invention are useful for monitoring human patients showing enhanced level of inflammation markers such as platelet count, mean platelet volume, erythrocyte sedimentation rate (ESR), serum thrombopoietin, serum erythropoietin, C-reactive protein and orosomucoid ($\alpha_1$-acid glycoprotein), TNF$\alpha$, Interleukins (notably IL1, IL2, IL6, IL8, IL10, IL15) as well as fecal markers of inflammation such as lactoferrin and calprotectin. Precise methods for diagnosing CD are detailed in Laas et al, 2014, which is incorporated herein by reference.

Also, the biological sample is preferably a stool sample, more preferably handled as described above.

In a preferred embodiment, the relative abundance of host DNA is determined as disclosed above.

The present inventors have found that these methods of the invention are highly sensitive and specific when the relative abundance of host DNA is determined and compared, directly or indirectly, to a reference value.

In a preferred embodiment, it can be concluded that the tested patient is suffering from unstable CD if the relative abundance of host DNA, as defined above, is higher than 10%, preferably higher than 18%, more preferably higher than 20%.

In a particular embodiment, the method of the invention comprises: performing at least one assay to determine host DNA relative abundance in a stool sample from a subject having or suspected of having Crohn disease in an unstable state, wherein the quantitative data represents host DNA relative abundance preferably compared to a reference value of about 10%.

In other words, the invention relates to an in vitro method for analysing a biological sample from a subject having or suspected of having Crohn disease in an unstable state, said method comprising the steps of:
a) Obtaining a stool sample from said subject,
b) Determining the relative abundance of host DNA in said sample, and,
c) Determining if said relative abundance is higher than a reference value of about 10%.

More precisely, in this particular embodiment, the in vitro diagnostic method of the invention enables to diagnose an unstable state of the Crohn disease in a human patient, comprising the following steps:
a) measuring the relative abundance of human DNA in a stool sample of said patient by any of the above-mentioned methods, and,
b) determining that said patient suffers from an unstable CD, if said relative abundance is higher than 10%.

Conversely, the present invention also allows the generation of quantitative data for a subject having or suspected of having Crohn disease (CD) in a stable state, or in other words the analysis of a biological sample from said subject, in particular for diagnosing a stable CD. In this case, it will be concluded that a subject suffers from an stable CD if the relative abundance of host DNA measured in a biological sample of said subject is higher than the reference value used for diagnosing CD (typically 1%), but lower than the reference value used for diagnosing an unstable state of the disease (typically 10%).

The methods of the invention can include (or exclude) the steps consisting of obtaining the stool sample and extracting the nucleic acid molecule from said sample, as defined above.

In principle, stool samples of subjects being in a quiescent (inactive) CD have a relative abundance of host DNA comprised between 0 and 10% (depending on the measurement technology for example). Yet, the presence of an intermediate level of host DNA (typically between 1% and 10%) in the stool samples of a subject is a hint that said subject may suffer from CD and that said CD is in a quiescent state. Moreover, the presence of a high level of host DNA (typically superior to 10%) in the stool samples of a subject is a hint that said subject may suffer from CD and that said CD is in an active state. The present invention therefore encompasses all methods aimed at diagnosing the state of CD in a subject, involving the detection of the presence of host DNA in stool samples. In other words, any diagnostic method involving the use of host DNA as biomarker of CD state is encompassed within the present invention.

Methods of Measures, in Particular to Design a Treatment

In another embodiment, the diagnostic methods of the invention can be used for adapting a treatment for a subject suffering from the Crohn disease.

In this embodiment, the methods of the invention therefore comprise the additional step of designing a treatment for the diagnosed subject, said treatment being adapted to the particular state of CD which has been diagnosed (such as by the method of the invention).

Thus, according to this aspect, the invention relates to a method for treating a subject suffering from Crohn disease, comprising:
i) generating quantitative data for a subject having or suspected of having Crohn disease (CD) in an unstable or stable state, according to the above-mentioned method, and
ii) treating said subject with an appropriate treatment, said appropriate treatment being chosen in those classically attributed by the practitioner.

In other words, the invention relates to a method for treating subject suffering from Crohn disease, comprising:
i) analysing a biological sample from a subject having or suspected of having Crohn disease in an unstable or stable state, according to the above-mentioned method, and
ii) treating said subject with an appropriate treatment, said appropriate treatment being chosen in those classically attributed by the practitioner.

More preferably, the invention encompasses a method for treating a subject suffering from Crohn disease, said method comprising the following steps:
i) diagnosing the activity of CD in a subject according to the above-mentioned method, and
ii) treating said subject with an appropriate treatment, said appropriate treatment being chosen in those classically attributed by the practitioner once said state of CD is diagnosed.

For example, if a CD patient is diagnosed in an unstable state, an adapted treatment can be a pharmacological treatment chosen in the group consisting of: azathioprine, mesalamine, abatacept, adalimumab, anakinra, certolizumab, etanercept, golimumab, infliximab, rituximab, tocilizumab, natalizumab, corticosteroids, cyclosporine, methotrexate, tacrolimus, Anti-JAK (tofacitinib), anti-integrins (Vedolizumab, rhuMAb Beta7, MAdCAM-1 Antagonist), or Anti IL12/IL23 (Ustekinumab, ABT874).

Alternatively, if a Crohn patient is diagnosed in a stable state, an adapted treatment will be lifestyle interventions, for example diets of different caloric restriction intensities and macronutrient composition (low carbohydrate, low fat, saturated fat diets).

Moreover, it is possible to use the methods of the invention for testing the efficiency of a treatment in a subject suffering from CD, in particular CD in an unstable state, or to evaluate the response of a patient to a treatment.

In this embodiment, the method of the invention comprises the following steps:
i) generating quantitative data for a subject having or suspected of having Crohn disease (CD) in an unstable state, according to the above-mentioned method, before and after the administration of a treatment, and
ii) concluding that the treatment is efficient in said subject if the state before the administration of the treatment was unstable but becomes stable upon administration of the treatment In other words, the method of the invention comprises:
i) analysing a biological sample from a subject having or suspected of having Crohn disease in an unstable state, according to the above-mentioned method, before and after the administration of a treatment, and
ii) concluding that the treatment is efficient in said subject if the state before the administration of the treatment was unstable but becomes stable upon administration of the treatment More precisely, the method of the invention comprises:
i) diagnosing the activity of CD before and after the administration of a treatment, according to the above-mentioned method, and
ii) concluding that the treatment is efficient in said subject if the state before the administration of the treatment was unstable but becomes stable upon administration of the treatment If the Crohn patient is diagnosed to be "unstable" before the administration of the treatment and becomes "stable" upon administration of the treatment, then said patient is responding to said treatment. This efficient treatment should therefore be preferentially maintained.

Conversely, if the Crohn patient is diagnosed to be "unstable" before the administration of the treatment and remains "unstable" upon administration of the treatment, then said patient is not responding to said treatment, and it is better to replace said treatment with another one or to combine it with another treatment Of note, if the Crohn patient is diagnosed to be "stable" before the administration of the treatment, then it is not worth administering any chemical treatment, as lifestyle interventions could be sufficient.

Combined Methods of Measures, in Particular for Diagnosis

The present inventors furthermore propose to associate the measure of host DNA abundance with the measure of another biomarker commonly used to diagnose CD, and/or the state of CD (i.e., active vs quiescent state).

In a particular embodiment, the present invention is therefore drawn to a method for generating quantitative data for a subject having or suspected of having Crohn disease (CD), said method comprising:

a) performing at least one assay to determine host DNA relative abundance in a biological sample from said subject, wherein a first quantitative data represents host DNA relative abundance preferably compared to a reference value; and b) performing at least one assay to determine calprotectin level, or a combined clinical score, in another biological sample from said subject, wherein a second quantitative data represents said calprotectin level preferably compared to 150 µg/mL or said combined clinical score preferably compared to a predetermined score.

In other words, the invention relates to a method for analysing a biological sample from a subject having or suspected of having Crohn disease (CD), said method comprising:

a) Obtaining a biological sample from said subject,
b) Determining the relative abundance of host DNA in said sample,
c) Determining the calprotectin level, or a combined clinical score, in another biological sample from said subject, and,
d) Determining if said relative abundance is higher than a reference value, and if said calprotectin level is greater than 150 µg/mL or if said combined clinical score is higher than a predetermined score.

More precisely, the invention relates to a method for diagnosing Crohn disease (CD) in a subject comprising:

a) Obtaining a biological sample from said subject,
b) Determining the relative abundance of host DNA in said sample,
c) Determining the calprotectin level or a combined clinical score in another biological sample from said subject, and,
d) Diagnosing that said subject suffers from Crohn Disease, if said relative abundance is higher than a reference value, and if said calprotectin level is greater than 150 µg/mL or if said combined clinical score is higher than a predetermined score.

In a preferred embodiment, said reference value is of about 1%.

The skilled practitioner in the art would readily understand that the calprotectin level indicated in µg/mL (or in µg/g) refers to the calprotectin protein level, or in other words to the calprotectin protein expression level. Protein expression level can be assessed by any method well-known in the art, notably reviewed by Reeves et al. (2000) and Schena (2005). Those methods generally involve contacting a biological sample of interest with one or more detectable reagents that is or are suitable for measuring protein expression level, such as an antibody, and subsequently determining protein expression level based on the level of detected reagent, preferably after normalization. Examples of methods which generally involve the use of an antibody include, without limitation, Western blot, immunoblot, enzyme-linked immunosorbant assay (ELISA), enzyme-linked immunospot (ELISPOT), radioimmunoassay (RIA), immunohistochemistry and immunoprecipitation. Other methods suitable for measuring a protein expression level, which do not necessarily involve the use of an antibody, may be used, including, without limitation, fluorescence activated cell sorting (FACS), microscopy such as atomic force microscopy, flow cytometry, microcytometry, protein binding assay, ligand binding assay, microarray, polyacrylamide gel electrophoresis such as SDS-PAGE, surface plasmon resonance (SPR), Forster resonance energy transfer (FRET), Bioluminescence resonance energy transfer (BRET), chemiluminescence, fluorescent polarization, phosphorescence, mass spectrometry such as liquid chromatography mass spectrometry (LC-MS) or liquid chromatography/mass spectrometry/mass spectrometry (LC-MS-MS), matrix-assisted laser desorption/ionization time-of-flight (MALDI-TOF), surface-enhanced laser desorption/ionization time-of-flight (SELDI-TOF), and magnetic resonance imaging (MRI).

In another preferred embodiment, host DNA relative abundance and calprotectin level can be measured from the same biological sample of the subject Accordingly, the present invention further relates to a method for generating quantitative data for a subject having or suspected of having Crohn disease (CD), said method comprising:

a) performing at least one assay to determine host DNA relative abundance in a biological sample from said subject, wherein a first quantitative data represents host DNA relative abundance preferably compared to a reference value; and b) performing at least one assay to determine calprotectin level, or a combined clinical score, in said sample, wherein a second quantitative data represents said calprotectin level preferably compared to 150 µg/mL or said combined clinical score preferably compared to a predetermined score.

In other words, the invention relates to a method for analysing a biological sample from a subject having or suspected of having Crohn disease (CD), said method comprising:

a) Obtaining a biological sample from said subject,
b) Determining the relative abundance of host DNA in said sample,
c) Determining the calprotectin level, or a combined clinical score, in said sample, and,
d) Determining if said relative abundance is higher than a reference value, and if said calprotectin level is greater than 150 µg/mL or if said combined clinical score is higher than a predetermined score.

More precisely, the invention relates to a method for diagnosing Crohn disease (CD) in a subject comprising:

a) Obtaining a biological sample from said subject,
b) Determining the relative abundance of host DNA in said sample,
c) Determining the calprotectin level, or a combined clinical score, in said sample, and,
d) Diagnosing that said subject suffers from Crohn Disease, if said relative abundance is higher than a reference value, and if said calprotectin level is greater than 150 µg/mL or if said combined clinical score is higher than a predetermined score.

In a preferred embodiment, said reference value is of about 1%.

In a preferred embodiment, calprotectin is measured in stool samples of the tested subject. In a more preferred embodiment, host DNA and calprotectin detection as described above are performed from the same stool sample. This may nevertheless require conducting two separate types of detection, one for measuring host DNA relative abundance (e.g. by qPCR), and one for measuring calprotectin protein level (e.g. by ELISA).

Thus, in another aspect, the present invention proposes to measure the gene level of calprotectin, so that a single type of detection can be performed in the method of the invention. More preferably, such detection is performed in the same container, and even more preferably from the same biological sample, such as a stool sample.

In this regard, the inventors have herein surprisingly discovered that calprotectin protein and gene levels correlate with one another, even though the behaviour of these types of functional entities (i.e. gene and protein encoded by said gene) cannot be predicted from each other. Indeed, it is well-known in the art that, once transcribed, a protein expression level may still be regulated at the translation level, and that the corresponding protein can be subjected to posttranslational modifications, varying half-lives, and compartmentalization.

Thus, according to this aspect, the invention relates to a method for generating quantitative data for a subject having or suspected of having Crohn disease (CD), said method comprising:
a) performing at least one assay to determine host DNA relative abundance in a biological sample from said subject, wherein a first quantitative data represents host DNA relative abundance preferably compared to a first reference value; and
b) performing at least one assay to determine calprotectin gene level, or a combined clinical score, in said sample (preferred herein) or in another biological sample from said subject, wherein a second quantitative data represents said calprotectin gene level preferably compared to a second reference value or said combined clinical score preferably compared to a predetermined score.

In other words, the invention relates to a method for analysing a biological sample from a subject having or suspected of having Crohn disease (CD), said method comprising:
a) Obtaining a biological sample from said subject,
b) Determining the relative abundance of host DNA in said sample,
c) Determining the calprotectin gene level, or a combined clinical score, in said sample (preferred herein), or in another biological sample from said subject, and,
d) Determining if said relative abundance is higher than a first reference value, and if the calprotectin gene level is higher than a second reference value or if said combined clinical score is higher than a predetermined score.

More precisely, the invention relates to a method for diagnosing Crohn disease (CD) in a subject comprising:
a) Obtaining a biological sample from said subject,
b) Determining the relative abundance of host DNA in said sample,
c) Determining the calprotectin gene level, or a combined clinical score, in said sample (preferred herein) or in another biological sample from said subject, and,
d) Diagnosing that said subject suffers from Crohn Disease, if said relative abundance is higher than a first reference value, and if said calprotectin level is higher than a second reference value or if said combined clinical score is higher than a predetermined score.

In a preferred embodiment, said first reference value with regard to host DNA is as defined above, and more preferably is of about 1%.

Gene level, or gene expression level, can be measured by any method well-known in the art, such as the ones described above for measuring host and microbial DNA. Genes encoding calprotectin are well-known in the art. In particular, human calprotectin is known to form a heterodimer made of the S100 calcium binding protein A8 (S100A8, also known as calgranulin A) and the S100 calcium binding protein A9 (S100A9, also known as calgranulin B or migration inhibitory factor-related protein 14 (MRP14)). The nucleotide sequence of the human S100A8 gene is available under the Genbank accession number: CR407674, version number: CR407674.1, while the one of the human S100A9 gene is available under the NCBI Reference Sequence accession number: NM_002965, version number: NM_002965.3.

In a preferred embodiment, the second reference value is a specific value or dataset that can be used to identify samples that are known to belong to healthy subjects (i.e. not having Crohn disease). Said reference value can therefore be easily determined by the skilled practitioner. It can be a single cut-off value, such as a median or mean. It can be a single number, equally applicable to every sample. In a preferred embodiment, this reference is a predetermined value. By "higher than a second reference value", it is thus meant herein that calprotectin gene level is superior than said reference value.

A particularly preferred technique for measuring host DNA relative abundance and/or calprotectin gene level is qPCR, using for example nucleic acid fragments (such as primers and/or probes) that are specific to the gene(s) encoding calprotectin.

By "combined clinical score", it is herein meant any score that combines biological parameters with clinical parameters to produce a score related to disease severity or mucosal healing in CD. It can be for example a combination of calprotectin levels (that are typically higher than 150 µg/mL in CD suffering patients), HBI (that is typically higher than 4 in CD suffering patients), gender, age, disease duration, platelet count, albumin, platelet, CRP, rectal bleeding (Abstract OP05, $7^{th}$ congress of ECCO).

By "predetermined score", it is herein meant a value resulting from a combination of multiple parameters through any statistical or algorithmic method (see, e.g., the parameters and values mentioned in Abstract OP05, 7th congress of ECCO). In some embodiments a predetermined score is 150m/mL for Calprotectin. In some embodiments a predetermined score is 4 for HBI.

In a further aspect, the present invention relates to a method for generating quantitative data for a subject having or suspected of having Crohn disease in an unstable state, said method comprising:
a) performing at least one assay to determine host DNA relative abundance in a biological sample from said subject, wherein a first quantitative data represents host DNA relative abundance preferably compared to a reference value; and
b) performing at least one assay to determine calprotectin level, or a combined clinical score, in another biological sample from said subject, wherein a second quantitative data represents said calprotectin level preferably compared to 250 µg/g, or said combined clinical score preferably compared to a predetermined score.

In other words, the invention relates to an in vitro method for analysing a biological sample from a subject having or suspected of having Crohn disease in an unstable state, said method comprising the steps of:
a) Obtaining a biological sample from said subject,
b) Determining the relative abundance of host DNA in said sample,
c) Determining the calprotectin level or a combined clinical score in another biological sample from said subject, and,
d) Determining if said relative abundance is greater than a reference value, and if said calprotectin level is greater than 250 µg/g or if said combined clinical score is higher than a predetermined score.

More precisely, the present invention relates to an in vitro method for diagnosing the activity of the Crohn Disease in a subject, comprising the steps of:

a) Obtaining a biological sample from said subject,
b) Determining the relative abundance of host DNA in said sample,
c) Determining the calprotectin level or a combined clinical score in another biological sample from said subject, and,
d) Diagnosing that said subject has a Crohn disease in an unstable state, if said relative abundance is greater than a reference value, and if said calprotectin level is greater than 250 µg/g or if said combined clinical score is higher than a predetermined score.

In a preferred embodiment, said reference value is of about 10%.

In another preferred embodiment, host DNA relative abundance and calprotectin level can be measured from the same biological sample of the subject Accordingly, the present invention further relates to a method for generating quantitative data for a subject having or suspected of having Crohn disease in an unstable state, said method comprising:
a) performing at least one assay to determine host DNA relative abundance in a biological sample from said subject, wherein a first quantitative data represents host DNA relative abundance preferably compared to a reference value; and
b) performing at least one assay to determine calprotectin level, or a combined clinical score, in said sample, wherein a second quantitative data represents said calprotectin level preferably compared to 250 µg/g, or said combined clinical score preferably compared to a predetermined score.

In other words, the invention relates to a method for analysing a biological sample from a subject having or suspected of having Crohn disease in an unstable state, said method comprising the steps of:
a) Obtaining a biological sample from said subject,
b) Determining the relative abundance of host DNA in said sample,
c) Determining the calprotectin level or a combined clinical score, in said sample, and,
d) Determining if said relative abundance is greater than a reference value, and if said calprotectin level is greater than 250 µg/g, or if said combined clinical score is higher than a predetermined score.

More precisely, the present invention relates to an in vitro method for diagnosing the activity of the Crohn Disease in a subject, comprising the steps of:
a) Obtaining a biological sample from said subject,
b) Determining the relative abundance of host DNA in said sample,
c) Determining the calprotectin level or a combined clinical score, in said sample, and,
d) Diagnosing that said subject has a Crohn disease in an unstable state, if said relative abundance is greater than a reference value, and if said calprotectin level is greater than 250 µg/g, or if said combined clinical score is higher than a predetermined score.

In a preferred embodiment, said reference value is of about 10%.

In a preferred embodiment, calprotectin is measured in stool samples of the tested subject. In a more preferred embodiment, host DNA and calprotectin detection as described above are performed from the same stool sample. This may nevertheless require conducting two separate types of detection, one for measuring host DNA relative abundance (e.g. by qPCR), and one for measuring calprotectin protein level (e.g. by ELISA).

Thus, in another aspect, the present invention proposes to measure the gene level of calprotectin, so that a single type of detection can be performed in the method of the invention. More preferably, such detection is performed in the same container, and even more preferably from the same biological sample, such as a stool sample.

Thus, according to this aspect, the invention relates to a method for generating quantitative data for a subject having or suspected of having Crohn disease in an unstable state, said method comprising:
a) performing at least one assay to determine host DNA relative abundance in a biological sample from said subject, wherein a first quantitative data represents host DNA relative abundance preferably compared to a first reference value; and
b) performing at least one assay to determine calprotectin gene level, or a combined clinical score, in said sample (preferred herein) or in another biological sample from said subject, wherein a second quantitative data represents said calprotectin gene level preferably compared to a second reference value, or said combined clinical score preferably compared to a predetermined score.

In other words, the invention relates to a method for analysing a biological sample from a subject having or suspected of having Crohn disease (CD) in an unstable state, said method comprising:
a) Obtaining a biological sample from said subject,
b) Determining the relative abundance of host DNA in said sample,
c) Determining the calprotectin gene level, or a combined clinical score, in said sample (preferred herein) or in another biological sample from said subject, and,
d) Determining if said relative abundance is higher than a first reference value, and if the calprotectin gene level is higher than a second reference value or if said combined clinical score is higher than a predetermined score.

More precisely, the invention relates to a method for diagnosing Crohn disease (CD) in an unstable state in a subject comprising:
a) Obtaining a biological sample from said subject,
b) Determining the relative abundance of host DNA in said sample,
c) Determining the calprotectin gene level, or a combined clinical score, in said sample (preferred herein) or in another biological sample from said subject, and,
d) Diagnosing that said subject suffers from Crohn Disease in an unstable state, if said relative abundance is higher than a first reference value, and if said calprotectin gene level is higher than a second reference value or if said combined clinical score is higher than a predetermined score.

In a preferred embodiment, said first reference value with regard to host DNA is as defined above, and more preferably is of about 10%; and said second reference value with regard to calprotectin is preferably the calprotectin gene level observed in subjects having quiescent Crohn disease (i.e. having Crohn disease in a stable state).

In a further aspect, the present invention relates to a method for generating quantitative data for a subject having or suspected of having Crohn disease in a stable state, said method comprising:
a) performing at least one assay to determine host DNA relative abundance in a biological sample from said subject, wherein a first quantitative data represents host DNA relative abundance preferably compared to a reference value; and
b) performing at least one assay to determine calprotectin level, or a combined clinical score, in another biological sample from said subject, wherein a second quantitative data represents said calprotectin level preferably compared to 250 μg/g, or said combined clinical score preferably compared to a predetermined score.

In other words, the invention relates to an in vitro method for analysing a biological sample from a subject having or suspected of having Crohn disease in a stable state, said method comprising the steps of:
a) Obtaining a biological sample from said subject,
b) Determining the relative abundance of host DNA in said sample,
c) Determining the calprotectin level or a combined clinical score in another biological sample from said subject, and,
d) Determining if said relative abundance is greater than a reference value, and if said calprotectin level is lower than 250 μg/g, or if said combined clinical score is lower than a predetermined score.

More precisely, the invention relates to an in vitro method for diagnosing the activity of the Crohn Disease in a subject, comprising the steps of:
a) Obtaining a biological sample from said subject,
b) Determining the relative abundance of host DNA in said sample,
c) Determining the calprotectin level or a combined clinical score in another biological sample from said subject, and,
d) Diagnosing that said subject has a Crohn disease in a stable state, if said relative abundance is greater than a reference value, and if said calprotectin level is lower than 250 μg/g or if said combined clinical score is lower than a predetermined score.

In a preferred embodiment, said reference value is of about 1%.

In another preferred embodiment, host DNA relative abundance and calprotectin level can be measured from the same biological sample of the subject Accordingly, the present invention further relates to a method for generating quantitative data for a subject having or suspected of having Crohn disease in a stable state, said method comprising:
a) performing at least one assay to determine host DNA relative abundance in a biological sample from said subject, wherein a first quantitative data represents host DNA relative abundance preferably compared to a reference value; and
b) performing at least one assay to determine calprotectin level, or a combined clinical score, in said sample, wherein a second quantitative data represents said calprotectin level preferably compared to 250 μg/g, or said combined clinical score preferably compared to a predetermined score.

In other words, the invention relates to a method for analysing a biological sample from a subject having or suspected of having Crohn disease (CD) in a stable state, said method comprising:
a) Obtaining a biological sample from said subject,
b) Determining the relative abundance of host DNA in said sample,
c) Determining the calprotectin level or a combined clinical score, in said sample, and,
d) Determining if said relative abundance is greater than a reference value, and if said calprotectin level is lower than 250 μg/g or if said combined clinical score is lower than a predetermined score.

More precisely, the invention relates to a method for diagnosing Crohn disease (CD) in a stable state in a subject comprising:
a) Obtaining a biological sample from said subject,
b) Determining the relative abundance of host DNA in said sample,
c) Determining the calprotectin level or a combined clinical score in said sample, and,
d) Diagnosing that said subject has a Crohn disease in a stable state, if said relative abundance is greater than a reference value, and if said calprotectin level is lower than 250 μg/g, or if said combined clinical score is lower than a predetermined score.

In a preferred embodiment, said reference value is of about 1%.

In a preferred embodiment, calprotectin is measured in stool samples of the tested subject. In a more preferred embodiment, host DNA and calprotectin detection as described above are performed from the same stool sample. This may nevertheless require conducting two separate types of detection, one for measuring host DNA relative abundance (e.g. by qPCR), and one for measuring calprotectin protein level (e.g. by ELISA).

Thus, in another aspect, the present invention proposes to measure the gene level of calprotectin, so that a single type of detection can be performed in the method of the invention. More preferably, such detection is performed in the same container, and even more preferably from the same biological sample, such as a stool sample.

Thus, according to this aspect, the invention relates to a method for generating quantitative data for a subject having or suspected of having Crohn disease in a stable state, said method comprising:
a) performing at least one assay to determine host DNA relative abundance in a biological sample from said subject, wherein a first quantitative data represents host DNA relative abundance preferably compared to a first reference value; and
b) performing at least one assay to determine calprotectin gene level, or a combined clinical score, in said sample (preferred herein) or in another biological sample from said subject, wherein a second quantitative data represents said calprotectin level preferably compared to a second reference value and/or to a third reference value, or said combined clinical score preferably compared to a predetermined score.

In other words, the invention relates to a method for analysing a biological sample from a subject having or suspected of having Crohn disease (CD) in a stable state, said method comprising:
a) Obtaining a biological sample from said subject,
b) Determining the relative abundance of host DNA in said sample,
c) Determining the calprotectin gene level, or a combined clinical score, in said sample (preferred herein), or in another biological sample from said subject, and,
d) Determining if said relative abundance is higher than a first reference value, and if the calprotectin gene level is lower than a second reference value and/or higher than a third reference value or if said combined clinical score is lower than a predetermined score.

More precisely, the invention relates to a method for diagnosing Crohn disease (CD) in a stable state in a subject comprising:
a) Obtaining a biological sample from said subject,
b) Determining the relative abundance of host DNA in said sample,
c) Determining the calprotectin gene level, or a combined clinical score, in said sample (preferred herein), or in another biological sample from said subject, and, d) Diagnosing that said subject suffers from Crohn Disease in a stable state, if said relative abundance is higher than a first reference value, and if said calprotectin level is lower than a second reference value and/or higher than a third reference value or if said combined clinical score is lower than a predetermined score.

In a preferred embodiment, said first reference value with regard to host DNA is as defined above for a stable state (1%); said second reference value with regard to calprotectin is preferably the calprotectin gene level observed in subjects having active Crohn disease (i.e. having Crohn disease in an unstable state); and/or said third reference value with regard to calprotectin is preferably the calprotectin gene level observed in healthy subjects (i.e. not having Crohn disease).

These methods can be applied to any subject, either human or animal. Yet, in a preferred embodiment, they are applied to a human patient, in particular to a human that is suspected of suffering from CD, or is in need of a confirmation of having CD, or has been diagnosed for CD.

The biological sample used in the method of the invention is preferably a stool sample.

In a preferred embodiment, the relative DNA abundance is determined by using profiling methods based on hybridization analysis of polynucleotides, and/or sequencing of polynucleotides described above.

As indicated above, the calprotectin level is measured according to any method commonly known by the one of skill in the art. Preferably, calprotectin protein level can be expressed in µg/mL, or in µg/g.

These methods have significant advantages over the prior art, in particular compared with those involving the measure of calprotectin level in stool samples alone. Indeed, as known from the one of skill in the art, such diagnostic methods are not sensitive enough, and give false positive results.

Moreover, it has been observed by the Inventors that the two measures (step b) and step c)) do not reflect a simple correlation: the percent of human DNA is significantly increased in the samples with calprotectin higher than 150 µg/mL reflecting the fact that there is more human DNA present in the stool of patients having signs of gut inflammation. Therefore, although the two measures relate they do not seem to capture exactly the same clinical characteristics of clinical disease.

A preferred technique for measuring host DNA relative abundance and calprotectin gene level is qPCR.

Kits for Use in the Methods of the Invention

The methods described above may be performed, for example, by using prepackaged kits, comprising or consisting of the nucleic acid fragments of the invention.

The invention is thus directed to a kit for use in any method of the invention, said kit comprising, or consisting of:

a) at least one nucleic acid fragment hydridizing specifically with host DNA; and
b) instructions for performing said method.

As used herein, the term "instructions" refers to a publication, a recording, a diagram, or any other medium which can be used to communicate how to perform a method of the invention. Said instructions can, for example, be affixed to a container which contains said kit. Preferably, the instructions for using said kit include a reference value.

According to a preferred embodiment, said nucleic acid fragment hydridizing specifically with host DNA is selected from the group of the nucleic acid fragments of sequence SEQ ID NO:1 to SEQ ID NO:6, variants thereof and complementary sequences thereof, More preferably, said kit comprises, or consists of:
a) the primer set (SEQ ID NO:1, SEQ ID NO:2) and the probe of sequence SEQ ID NO:3; and/or the primer set (SEQ ID NO:4, SEQ ID NO:5) and the probe of sequence SEQ ID NO:6; and
b) instructions for performing said method.

Yet, even more preferably, the above kit can further comprise:
c) at least one reagent capable of specifically determining calprotectin protein or gene level.

The term "reagent capable of specifically determining calprotectin level" or "reagent capable of specifically determining calprotectin expression level" designates a reagent or a set of reagents which specifically recognizes calprotectin and allows for the quantification of the expression level thereof, at the protein or gene level. These reagents can be for example antibodies, aptamers or affibodies specifically recognizing the protein calprotectin, or nucleic acid fragments such as primers and/or probes recognizing the gene(s) encoding calprotectin. In the context of the present invention, such reagent is said to be "specific" for calprotectin or "recognizes specifically" calprotectin if it 1) exhibits a threshold level of binding and/or hybridizing activity, and/or 2) does not significantly cross-react with target molecules known to be related to calprotectin. The binding affinity of such reagent can be easily determined by one skilled in the art, for example, by Scatchard analysis. Cross-reactivity of a reagent can as well be easily determined by one skilled in the art, and thus need to be further detailed herein. Examples of reagents capable of specifically determining the expression level of calprotectin include, without limitation, anti-calprotectin antibodies (such as the MAC387 IgG1 from Invitrogen) and nucleic acid fragments hydridizing specifically with gene(s) encoding calprotectin, such as the S100A8 and/or S100A9 genes as described above.

The invention further relates to the use (in particular in vitro use) of the kit as described above, in any method of the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to "quantitative data" or a "primer" or a "probe" or "reagent" or "detectable reagent" includes a plurality of such data, primers, probes, reagents, detectable reagents, and so forth.

As used herein, numerical values are often presented in a range format throughout this document. The use of a range format is merely for convenience and brevity and should not be construed as an inflexible limitation on the scope of the invention. Accordingly, the use of a range expressly includes all possible subranges, all individual numerical values within that range, and all numerical values or numerical ranges include integers within such ranges and fractions of the values or the integers within ranges unless the context clearly indicates otherwise. This construction applies regardless of the breadth of the range and in all contexts throughout this patent document The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

A number of embodiments of the invention have been described.

Nevertheless, it will be understood that various modifications may be made without departing from the spirit and scope of the invention. Accordingly, the following examples are intended to illustrate but not limit the scope of invention described in the claims.

EXAMPLES

Example 1

1. Material and Methods
1.1. Cohort
1.1.1 CD Cohort

All participants were part of the "CrohnOmeter 1" study, which aim was to collect stool samples from a diverse population of Crohn Disease patients to investigate their gut microbiome. The inclusion criteria into the study were a clinical diagnosis of Crohn Disease and the participants signed an informed consent form. CrohnOmeter 1 is a longitudinal study, on average each participant provided 8 stool samples over an 8 months period of time. A total of 99 participants were included and provided stool samples. Out of the 99 participants, 68 had their stool samples sequenced. In total 438 samples were sequenced.

Each study participant filled in a questionnaire each time a stool sample was provided into the study. The questionnaire captured information on the patient's health and stool characteristics. In particular the following information was used to evaluate the state of disease activity/inflammatory status:

The calprotectin level (dosed in patient stools) was measured (calprotectin is a protein marker highlighting inflammation);

The Harvey-Bradshaw index (HBI) of each patient is recorded. HBI is a composite auto-evaluated index reflective of the general health status of the patient. The score is based on an evaluation of general well-being, an evaluation of abdominal pain, the number of liquid stools per day, the presence of abdominal mass and the presence of complications. It is widely spread for the evaluation of Crohn patient status.

1.1.2 Healthy Control Cohort

A control group of individuals was assembled from healthy individuals. Main exclusion criteria were the use of prescription medication and history of significant disease. Multiple samples were collected from the same individuals leading to a total of 137 samples.

1.1.3 NASH Control Cohort

An additional two NASH patients from a larger study were sequenced. The aim of the larger NASH study, called NASH2, was to collect stool samples from a diverse population of NASH patients to investigate their gut microbiome and identify differences between NASH and simple steatosis patients. 6 samples were available from those 2 patients. This cohort although small, was selected as a control population for an inflammatory disease not localized in the gut 1.2. Sample Collection and Preparation
1.2.1. Fecal Sampling The subjects from the CD cohort were provided dedicated collection kits containing a DNA stabilizer and written instructions every three weeks for the collection of a stool sample from their home. Upon collection of two, approx. 1 gram aliquots in a validated DNA preservation buffer (typically RNA Later®), the tubes containing the samples were shipped by regular post to the laboratory. One tube was directly stored at −80° C. as a stool suspension backup. The second tube was used for DNA extraction: three aliquots were prepared from the stool material using high speed centrifugation. These three aliquots were then stored at −80° C. before DNA extraction.

The same collection kit was used for the control cohorts.

1.2.2. DNA Extraction

A frozen aliquot of each fecal sample was suspended in 2500, of guanidine thiocyanate 0.1 M Tris (pH 7.5) and 40 µL of 10% N-lauroyl sarcosine. The suspension was then submitted to vigorous bead-beating to release DNA from microbial cells and DNA extraction was conducted using standard protocol (Godon et al, 1997). The DNA integrity and concentration were evaluated by Nanodrop and Agilent and on agarose gel electrophoresis.

1.3. Illumina Sequencing

The sequencing was performed at an ISO17025 accredited laboratory on a HiSeq 2500 Illumina sequencer. They used ISO 17025-accredited method HSHOv4 PE100. DNA library preparation followed the manufacturer's instruction (Illumina). The workflow indicated by the sequencing device provider was used to perform the different steps: cluster generation, template hybridization, isothermal amplification, linearization, blocking and denaturing and hybridization of the sequencing primers. The base-calling was performed using the provider's pipeline. The target of 40 million minimum paired-end reads were generated for each sample. Sequencing read length was 100 bp.

1.4 Bioinformatics Processing

The raw reads were processed using Enterome's in house pipeline. Briefly the pipeline is based on MOCAT (Kultima et al., 2012) and a compilation of internal scripts. It consists of quality controls, mapping and calculation of gene abundance using MOCAT v1.3, including list of Illumina adapters and human genome (hg19). The number of reads mapping to the human genome is based on 95% identity on 90% of the length and are returned after the quality controls steps that includes trimming bases with a low quality score. The percent of human reads in a sample is calculated using 1−number of reads mapping to hg19/number of reads after trimming.

2. Results 2.1. Comparison Between Controls Versus Crohn Disease Patients (CD)

Using the Wilcoxon rank sum test, we compared the 137 samples from healthy controls, 6 from NASH patients to the 438 samples from CD patients. The p-value was highly significant for CD versus healthy controls (p-value=1.667e−12), FIG. 1. Summary statistics for the two cohorts are provided in Table 1.

TABLE 1

Summary statistics for percent of reads mapping to the Human genome HG19.

| Cohort | Min. | 1stQu. | Median | Mean | 3rdQu. | Max. |
|---|---|---|---|---|---|---|
| CD | 0.0000282 | 0.0003732 | 0.0009794 | 0.0318600 | 0.0036770 | 0.8986000 |
| Healthy | 1.278e−05 | 1.822e−04 | 3.998e−04 | 8.975e−04 | 7.883e−04 | 1.012e−02 |
| NASH | 0.0007524 | 0.0009039 | 0.0011470 | 0.0021420 | 0.0014250 | 0.0074630 |

99% of samples from healthy controls had all less than 1% human DNA in their total stool DNA, compared to 84% of Crohn samples. Thus with a cutoff value of 1%, 16% of Crohn samples could be captured. The presence of DNA in the stool is thus highly specific.

2.2. Association to Disease Severity in Crohn Disease Patients (CD)

Since there is a highly significant difference between Crohn Disease patients and healthy controls in terms of percent of human DNA in the stool sample, the relation to disease severity was studied, to assess whether the measure of host DNA relative abundance could be used as a biomarker of disease activity.

To that end, patients were classified into disease active groups according to three criteria: 1) whether they had a calprotectin level above 150, 2) whether they had an HBI score above 4, 3) whether they had an HBI score above 4 or their calprotectin level above 150 (combined score)

Figure 2:
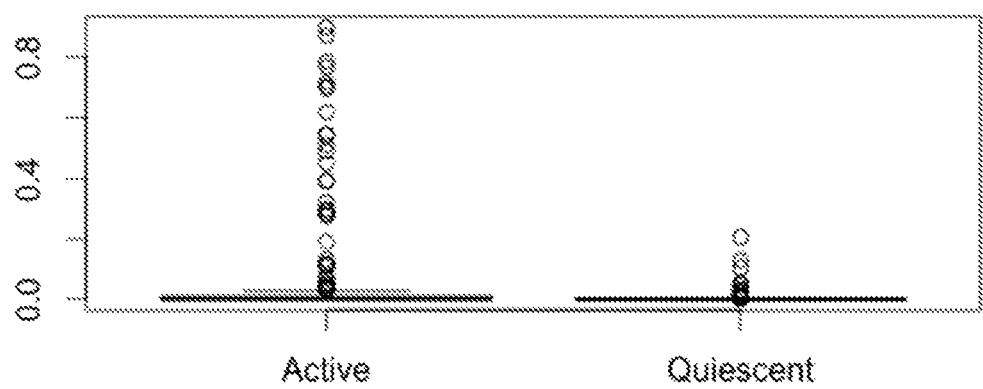
FIG. 2 discloses the relative abundance levels (in %) of the Host DNA found in the studied stool samples, both for Crohn disease patients in an active phase of the disease (on the left) and in a quiescent phase (on the right). The status of the disease (active phase vs quiescent phase) were determined using the combined score of calprotectin level and HBI score.

The difference, based on the Wilcoxon rank sum test, between percent (relative abundance) of human DNA in stool samples from patients in a quiescent (n=227) versus in stool samples of patients in an active phase of CD (n=211) was highly significant (see FIG. 2, P-val=1.034e−09).

95.5% of the samples with more than 20% human DNA were from active patients.

90% of the samples with more than 10% human DNA were from active patients.

80% of the samples with more than 1% human DNA were from active patients.

Figure 4:
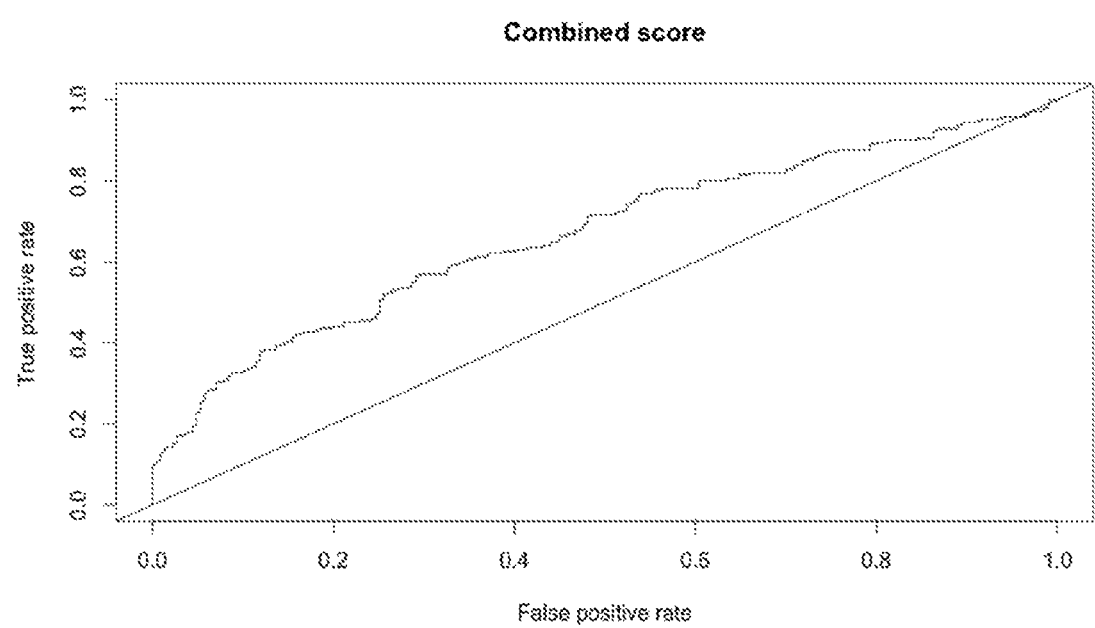
FIG. 4 discloses ROC curve using the percent of human DNA as a predictive score of disease activity within a CD population. The AUC has a value of 0.67 for the combined score.

The ROC curve (FIG. 4) is a visual representation, indicating the number of true and false positives based on various cut offs. As can be seen in the bottom left corner, there is a very high specificity (100%, but a low sensitivity, only about 10% of patients are captured). The straight line represents a "non informative" score.

Figure 3:
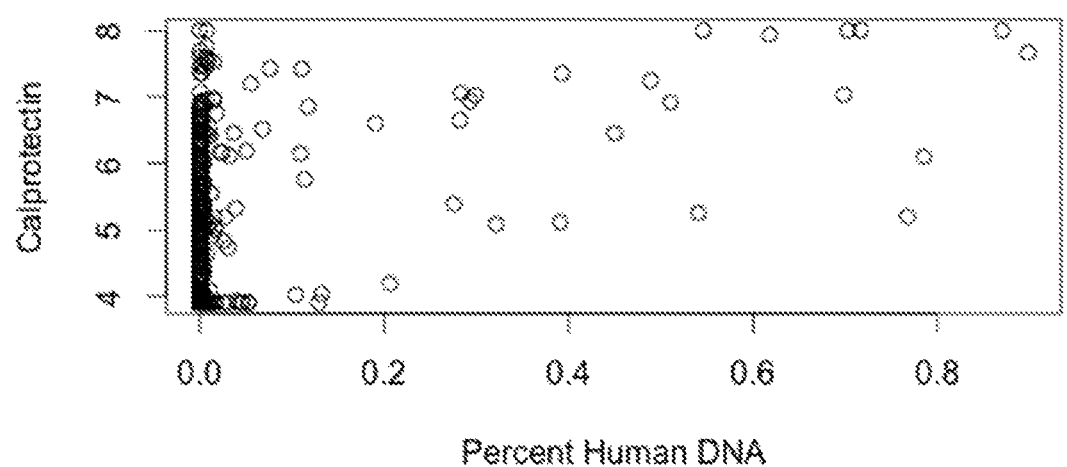
FIG. 3 discloses the percentage of human DNA versus calprotectin levels found in the studied stool samples.

Looking at calprotectin levels on its own and comparing it to human DNA (FIG. 3), the two measures do not reflect a simple correlation however, the percent of human DNA is significantly increased in the samples with calprotectin higher than 150 μg/ml (P-value=1.041e−07) reflecting the fact that there is more Human DNA present in the stool of patients having signs of gut inflammation. Interestingly, although the two measures relate they do not seem to capture exactly the same clinical characteristics of clinical disease since, as can be seen from the FIG. 3, some samples have very high calprotectin levels and no human DNA.

Example 2

1. Material and Methods
1.1. Cohort

Participants were part of the "CrohnOmeter 1" study, as described above. In total 11 stool samples were sequenced. The cohort fulfilled the same criteria as the one of Example 1.

1.2. Sample Collection and Preparation
1.2.1. Fecal Sampling and DNA Extraction

Fecal sampling and DNA extraction were performed, according to a similar procedure as the one detailed in Example 1 above.

1.2.2. qPCR Performed on Host DNA

The eleven samples were analyzed with the ValidPrime® assay (TATAA Biosciences) and run in triplicates. ValidPrime is highly optimized and specific to a non-transcribed locus of genomic DNA that is present in exactly one copy per haploid normal genome.

The primers were run in a final concentration of 400 nM and probe had a final concentration of 200 nM.

A standard curve spanning 100 000 copies to 6.10 copies per reaction was run together with the samples, dilution factor between standards was 4×. Samples were normalized to a concentration of 4.84 ng/μl which was at least a 10× dilution.

TABLE 2

Primers and probes for qPCR quantification of host DNA

| Primers and probes | Nucleotide sequence from 5' to 3' (SEQ ID NO:) |
|---|---|
| VP5 forward | AACTTGGTGCGGAGGT (SEQ ID NO: 1) |
| VP5 reverse | ATCGCTTCTGATGGACAC (SEQ ID NO: 2) |
| VP5 probe | CCGCCAGACTGCAATCCATCAATGACA (SEQ ID NO: 3) |
| VP9 forward | GCGGAAACACAAGGGAA (SEQ ID NO: 4) |
| VP9 reverse | TTAGAGGCAAAAGCAAAGAA (SEQ ID NO: 5) |
| VP9 probe | ACAGCTAATTAAAATTGCACAGTTCCT (SEQ ID NO: 6) |

Data, Cq-Values, from CFX manager software (Bio-Rad) was generated using threshold method. Threshold was set to 230. Standard curves were obtained from CFX manager software (Bio-Rad). Sample concentrations were calculated in the CFX manager using the standard curves.

1.2.3. Statistical Analysis of qPCR Data

The percentage of human DNA estimated was calculated based on the number of reads mapping to the human genome divided by the total number of reads in the sample. This percentage was correlated to the quantification of human DNA using the ValidPrime assays.

The ability to predict the value of a variable (human DNA) using the values of another variable (qPCR assay) was typically determined from a linear regression analysis of the data, assuming there is a linear response between the two variables. The statistical analysis was performed in R.

2. Results
2.1. Quantification of Host DNA Abundance by qPCR Specific Primers

Figure 5:
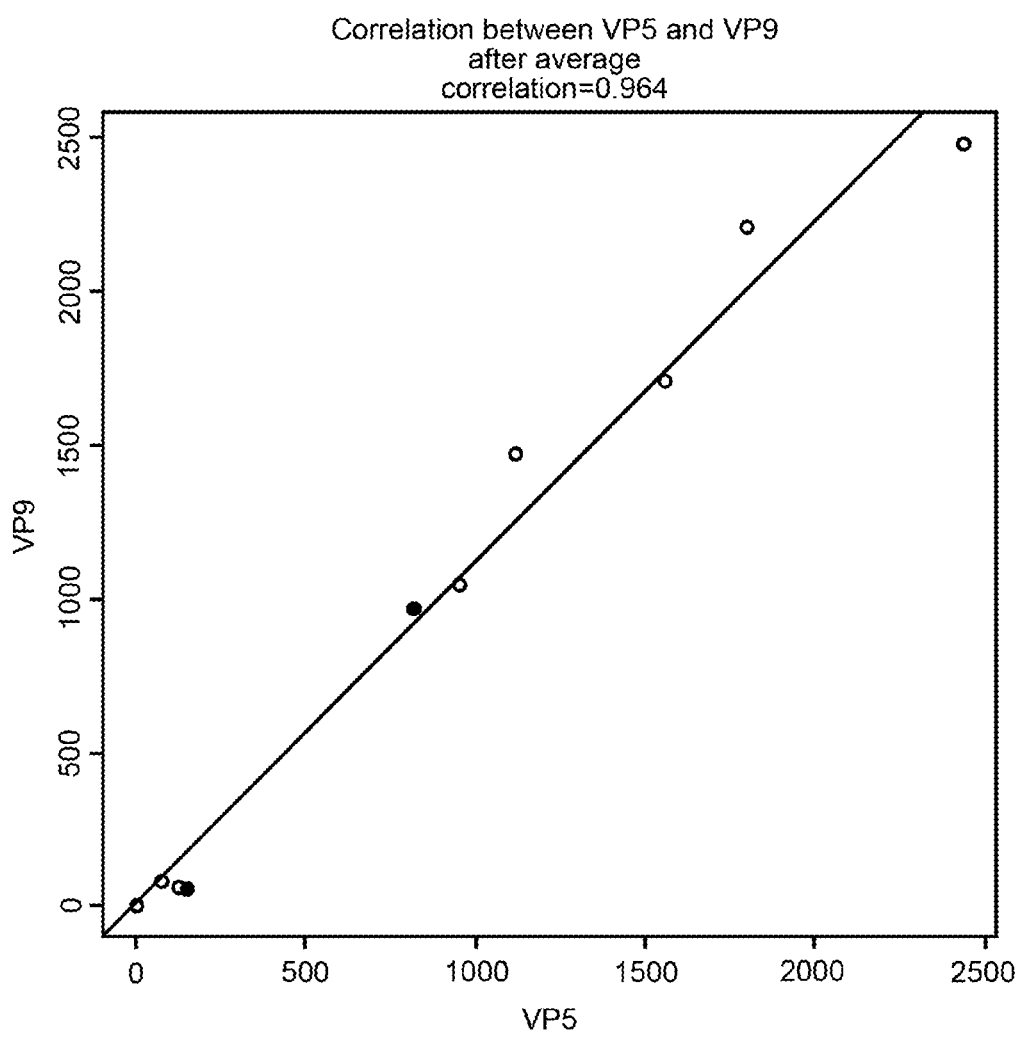
FIG. 5 discloses the correlation between the quantitative data of the VP5 and VP9 qPCR assays for measuring host DNA abundance.

FIG. 5 demonstrates a statistically significant correlation in the quantitative data generated between the qPCR assays performed using the VP5 and VP9 primers and probes (correlation=0.964).

Figure 6:
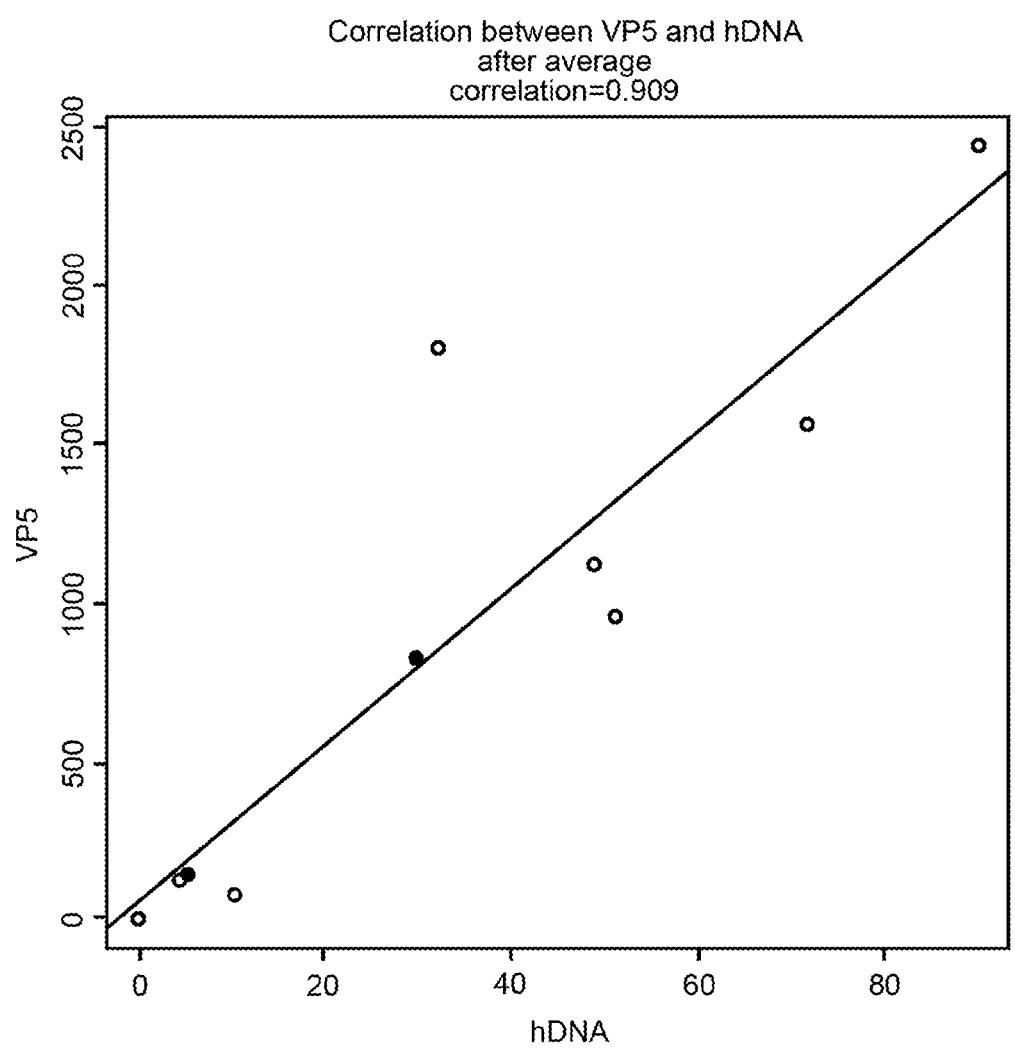
FIG. 6 discloses the correlation between the quantitative data of the VP5 qPCR assay and the percentage of human DNA relative abundance measured by Illumina sequencing.
Figure 7:
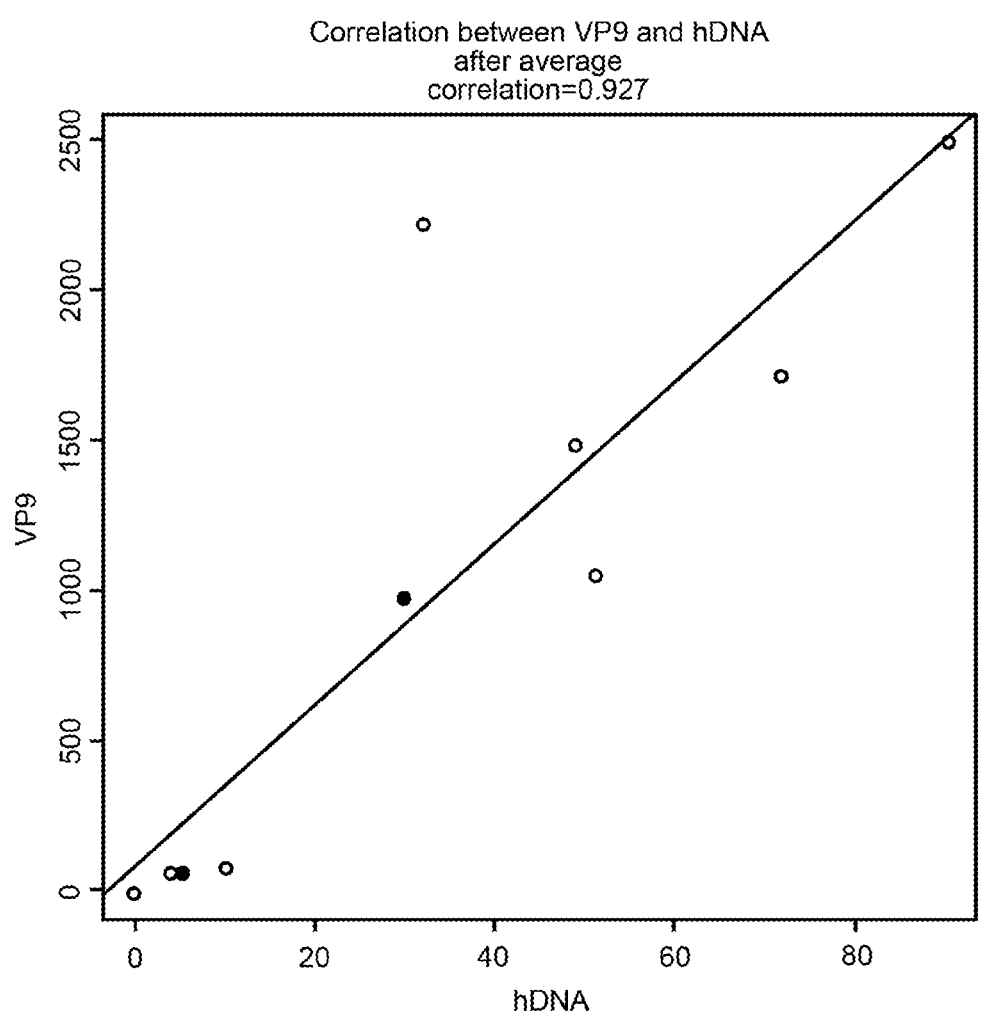
FIG. 7 discloses the correlation between the quantitative data of the VP9 qPCR assay and the percentage of human DNA relative abundance measured by Illumina sequencing.

FIGS. 6 and 7 show a statistically significant correlation in the quantitative data generated by the qPCR assay performed using the VP5 (FIG. 6) or the VP9 (FIG. 7) primers and probes, and the percentage of human DNA measured by the method proposed in Example 1 (i.e. Illumina sequencing) (correlation=0.909 for VP5 assay, and 0.927 for VP9 assay).

Accordingly, the measure of host DNA abundance by qPCR, using the VP5 and VP9 primers and probes described above in Table 2, can allow for the diagnosis of Crohn disease, and monitoring of the activity of said disease.

Example 3

1. Material and Methods
1.1. Cohort

Participants were part of the "CrohnOmeter 1" study, as described above. In total 15 stool samples were sequenced. The cohort fulfilled the same criteria as the one of Example 1.

1.2. Sample Collection and Preparation
1.2.1. Fecal Sampling and RNA Extraction

Fecal sampling was performed, according to the procedure detailed in Example 1 above The stool samples were then extracted with PowerMag® Microbiome RNA/DNA Isolation Kit (Cat No 27500-4-EP, MOBIO Laboratories, Inc) according to manufacturer's instructions, with a few modifications. Briefly, 650 µl lysis buffer and 100 µl phenol:chloroform:isoamyl alcohol were added directly to the stool samples. As much as possible was transferred to the glass bead plate. A homogenizer (Tissuelyser II, Qiagen) was run at 30 Hz for 2×5 min. After transferring the supernatant, an extra bead beating step was performed. The volumes added to the pellet were 300 µl lysis buffer and 45 µl phenol:chloroform:isoamyl alcohol. 220 µl of inhibitor removal solution was added to the pooled supernatant and 450 µl total sample volume was further processed with KingFisher Flex (Thermo Scientific).

1.2.2. RNA Quality and Normalization

The absorbance and purity of the 15 extracted RNA/DNA samples were analyzed on a spectrophotometer (DropSense96, Trinean nv). The quality of the RNA was measured in RIN-values on gel electrophoresis (BioAnalyzer, Agilent Technologies). The samples were normalized to approximately 66.67 ng/µl based on the absorbance measurement 1.2.3. cDNA Synthesis All samples were reverse transcribed into cDNA using TATAA GrandScript cDNA Synthesis kit #A103 (TATAA Biocenter AB). Prior to cDNA synthesis a DNase treatment was performed using Heat&Run gDNA removal Kit (Cat No 80200-50, ArticZymes) according to manufacturer's instructions. Maximum load of RNA was added to the reaction to be able to retrieve as high Cq-values as possible. The reagents were mixed. Reverse transcription was performed in 20 µl reaction volume on T100 (Bio-Rad Laboratories, Inc). The temperature program in table 3 was applied for the cDNA synthesis.

1.2.4. qPCR

The 15 samples were diluted 9× after reverse transcription. qPCR was performed with TATAA Probe® GrandMaster Mix #TA02 (TATAA Biocenter AB) and the reagents were mixed. All samples including genomic DNA and a negative control were run in triplicates in 10 µl reactions on CFX384 platform (Bio-Rad). The samples were run on using 2 genes of interest (See Table 3), ValidPrime (for genomic DNA background correction) and B2M medium and short assays (for control of physical fragmentation, large delta Cq between those two assays will indicate degradation see Bjorkman, et al. (2016). The pipetting was performed by a pipetting robot (EpMotion 5070, Eppendorf, Germany). A 2-step temperature program was applied and detection was performed in the FAM channel.

qPCR was performed using primers and probes designed to amplify the S100A8 and S100A9 genes, which encode protein that form the heterodimer of calprotectin. Said primers and probes can be easily designed by the skilled practitioner based on the publicly available nucleotide sequence of these genes.

TABLE 3

| Genes encoding the S100A8 and S100A9 proteins | | |
|---|---|---|
| Gene Symbol | Protein encoded by said gene | Gene sequence |
| S100A8 | S100 calcium binding protein A8 | Genbank CR407674.1 |
| S100A9 | S100 calcium binding protein A9 | NCBI RefSeq NM_002965.3 |

Raw data was generated using threshold method on the CFX manager software (Bio-Rad). qPCR data was analyzed with GenEx software (MultiD Analyses AB) using reference gene validation with geNorm and NormFinder to evaluate the most stably expressed genes.

1.2.5. Statistical Analysis

For each gene, triplicate values were averaged. The Cq values along with the values normalized by house-keeping genes (delta Cq values), were compared to the log 10 transformed ELISA values obtained for measuring calprotectin protein level, (see Example 1, value of 150 µg/mL). The spearman correlation was computed. Additionally a cutoff of 250 µg/g was used to classify patients as inflamed or non inflamed (Dhaliwal et al., 2015) and a Wilcoxon rank test was performed on the Cq values for each gene to compare the two groups. The statistical analysis was performed in R.

2. Results
2.1. Quantification of Calprotectin Gene Level by qPCR Specific Primers S100A8 and S100A9 genes had Cq values for all 12 (S100A9) to 15 (S100A8) of the tested samples. Stati

TABLE 4

| Statistical data | | |
|---|---|---|
| Gene Symbol | Spearman Correlation | P-value |
| S100A8 | −0.72 | 0.0025 |
| S100A9 | −0.59 | 0.039 |

Figure 8:
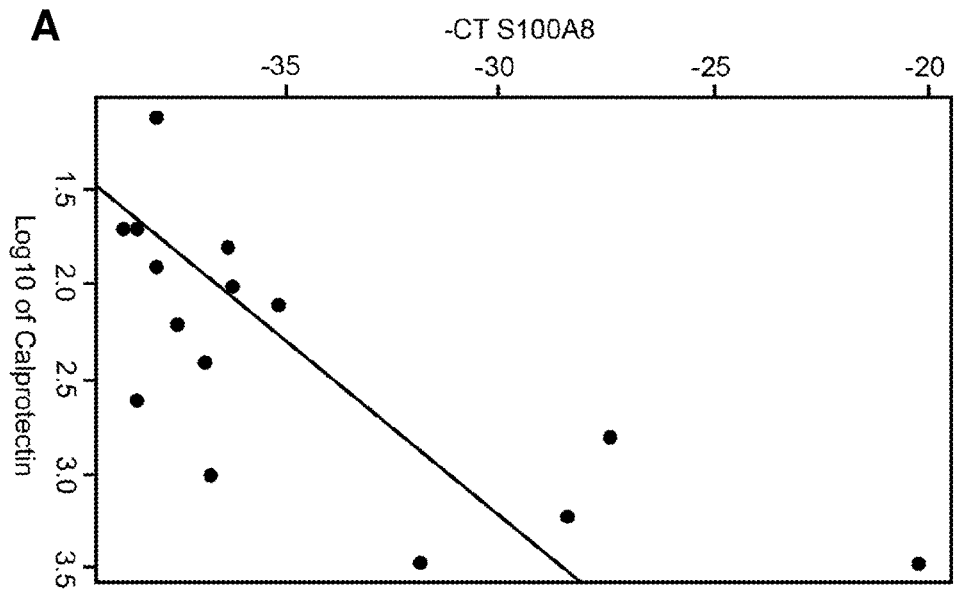
FIG. 8 discloses the correlation between mRNA level of faecal calprotectin by qPCR assay (measure of S100A8 and S100A9 mRNA level) and protein level of faecal calprotectin by ELISA (A: S100A8; B: S100A9).
Figure 8:
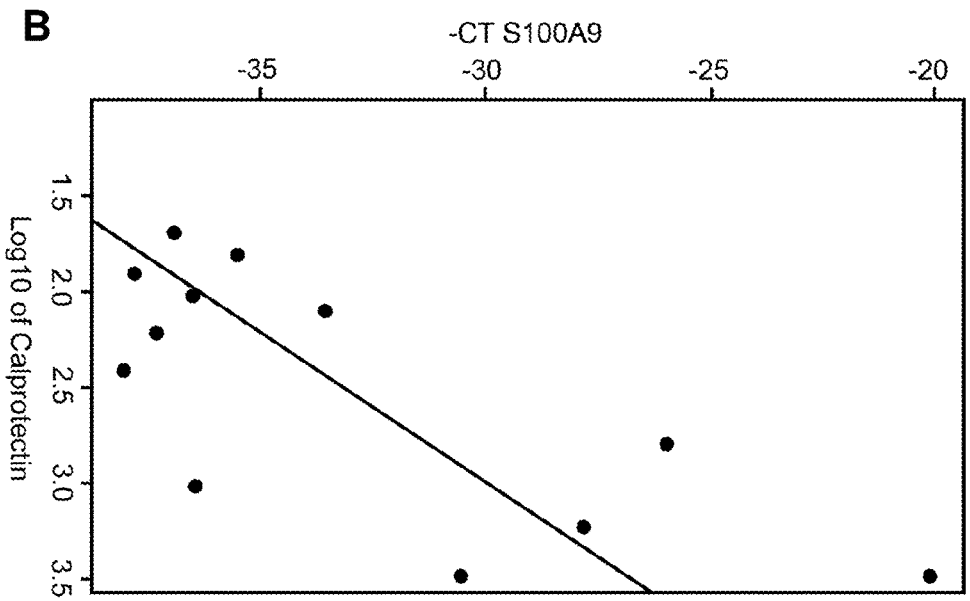

FIG. 8 shows a statistically significant correlation between faecal mRNA levels in genes S100A8 and S100A9 and faecal calprotectin level (protein level).

Accordingly, the measure of calprotectin gene level by qPCR, and more particularly of the S100A8 and/or S100A9 gene level, can allow for the diagnosis of Crohn disease, and more particularly for the monitoring of the activity of said disease, when preferably combined with the measure of host DNA relative abundance.

This test can further be easily performed in combination with the qPCR test for measuring host DNA abundance described in Example 2, preferably in a single test tube.

BIBLIOGRAPHIC REFERENCES

Cho, J. H., & Brant, S. R. (2011). Recent insights into the genetics of inflammatory bowel disease. *Gastroenterology*, 140(6), 1704-12. doi:10.1053/j.gastro.2011.02.046

HMP, A framework for human microbiome research. *Nature*. 2012 Jun. 13; 486(7402):215-21

Klaassen C H, Jeunink M A, Prinsen C F, Ruers T J, Tan A C, Strobbe L J, Thunnissen F B. Quantification of human DNA in feces as a diagnostic test for the presence of colorectal cancer. *Clin Chem.* 2003 July; 49(7):1185-7.

Laas et al. Diagnosis and classification of Crohn's disease. *Autoimmun Rev.* 2014 April-May; 13(4-5):467-71.

Molodecky N A, et al. Increasing incidence and prevalence of the inflammatory bowel diseases with time, based on systematic review. *Gastroenterology.* 2012 January; 142(1):46-54.e42; quize30. doi: 10.1053/j.gastro.2011.10.001.

Vincent C, Mehrotra S, Loo V G, Dewar K, Manges A R. Excretion of Host DNA in Feces Is Associated with Risk of *Clostridium difficile* Infection. *Journal of Immunology Research* 2014 September; Article ID 246203.

Shewale J G, Schneida E, Wilson J, Walker J A, Batzer M A and Sinha S K, Human Genomic DNA Quantitation System, H-Quant: Development and Validation for use in Forensic Casework; *Journal of Forensic Science,* 2007, vol. 52 (2)

Reeves J. R. and Bartlett J. M. S. Methods in Molecular Medicine; vol. 39, chapter 51, 471-483 (2000)

Schena M. Protein microarrays; Jones and Bartlett Learning. (2005)

Godon J J, Zumstein E, Dabert P, Habouzit F and Moletta R, Molecular microbial diversity of an anaerobic digestor as determined by small-subunit rDNA sequence analysis. *Appl. Environ. Microbiol.* 1997, 63(7):2802.

Parker R M & Barnes N M, mRNA: detection by in Situ and northern hybridization. *Methods in Molecular Biology* 106:247-283 (1999)

Heid C A, Stevens J, Livak K J, Williams P M., Real time quantitative PCR, *Genome Research* 6:986-994 (1996)

Kultima J R, Sunagawa S, Li J, Chen W, Chen H, Mende D R, Arumugam M, Pan Q, Liu B, Qin J, Wang J, Bork P.; MOCAT: a metagenomics assembly and gene prediction toolkit. *PLoS One.* 2012; 7(10):e47656

Björkmana J., Svec D., Lott E, Kubistaa M., and Sjobacka R. *Biomolecular Detection and Quantification;* 2016, volume 6: 4-12

Dhaliwal A., Zeino Z., Tomkins C., Cheung M., Nwokolo C., Smith S. Harmston C., and Arasaradnam R. P. *Frontline Gastroenterol;* 2015, 6(1):14-19. Epub

What is claimed is:

1. A method for treating a subject suffering from Crohn's disease (CD), comprising:
    providing a stool sample from a subject suffering from Crohn's disease, wherein the stool sample comprises subject DNA;
    performing an assay to quantify the relative abundance of subject DNA in the sample; and
    administering a CD treatment to the subject when the relative abundance of the subject DNA is above 1%.

2. The method of claim 1, further comprising:
    preparing protein from the stool sample; and
    measuring a level of calprotectin protein in the stool sample.

3. The method of claim 2, further comprising determining if the calprotectin protein level is higher than a reference level.

4. The method of claim 3, wherein the reference level is 150 µg/mL of caiprotectin protein.

5. The method of claim 1, wherein the method does not comprise an endoscopic evaluation of the subject.

6. The method of claim 1, wherein the treatment is selected from the group consisting of azathioprine, mesalamine, abatacept, adalimumab, anakinra, certolizumab, etanercept, golimumab, infliximab, rituximab, tocilizumab, natalizumab, corticosteroids, cyclosporine, methotrexate, tacrolimus, Anti-JAK (tofacitinib), anti-integrins (Vedolizumab, rhuMAb Beta7, MAdCAM-1 Antagonist), and Anti IL12/IL23 (Ustekinumab, ABT874).

7. The method of claim 1, wherein the treatment is a diet of different caloric restriction intensities and macronutrient composition.

* * * * *